United States Patent
Mohapatra et al.

(10) Patent No.: US 9,618,501 B2
(45) Date of Patent: *Apr. 11, 2017

(54) THREE-DIMENSIONAL FIBROUS SCAFFOLDS FOR CELL CULTURE

(71) Applicant: University of South Florida, Tampa, FL (US)

(72) Inventors: Subhra Mohapatra, Tampa, FL (US); Shyam S. Mohapatra, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/447,779

(22) Filed: Jul. 31, 2014

(65) Prior Publication Data
US 2015/0024967 A1 Jan. 22, 2015

Related U.S. Application Data

(63) Continuation-in-part of application No. 13/775,536, filed on Feb. 25, 2013.

(60) Provisional application No. 61/602,337, filed on Feb. 23, 2012, provisional application No. 61/723,922, filed on Nov. 8, 2012, provisional application No. 61/861,632, filed on Aug. 2, 2013.

(51) Int. Cl.
*C12N 5/09* (2010.01)
*G01N 33/50* (2006.01)
*C12N 5/00* (2006.01)

(52) U.S. Cl.
CPC ....... *G01N 33/5011* (2013.01); *C12N 5/0068* (2013.01); *C12N 5/0693* (2013.01); *C12N 2533/40* (2013.01); *C12N 2533/72* (2013.01); *G01N 2500/10* (2013.01)

(58) Field of Classification Search
None
See application file for complete search history.

(56) References Cited

U.S. PATENT DOCUMENTS

| | | | |
|---|---|---|---|
| 2004/0018226 A1* | 1/2004 | Wnek | A61F 2/08 424/443 |
| 2008/0113390 A1 | 5/2008 | Han et al. | |
| 2010/0068285 A1* | 3/2010 | Zale | A61K 9/10 424/489 |
| 2010/0304989 A1 | 12/2010 | Von Hoff et al. | |

(Continued)

FOREIGN PATENT DOCUMENTS

WO 2010028288 A2 3/2010

OTHER PUBLICATIONS

Ivascu et al. "Diveristy of cell-mediated adhesions in breast cancer spheroid" International Journal of Oncology 31: 1403-1413, 2007.*

(Continued)

*Primary Examiner* — Blaine Lankford
*Assistant Examiner* — Lauren K Van Buren
(74) *Attorney, Agent, or Firm* — Thomas | Horstemeyer, LLP

(57) ABSTRACT

Provided herein is a three-dimensional scaffold composition comprising randomly oriented fibers, wherein the fibers comprise a polyethylene glycol-polylactic acid block copolymer (PEG-PLA) and a poly(lactic-co-glycolic acid) (PLGA). Also provided are methods for using the three-dimensional scaffolds described herein.

8 Claims, 18 Drawing Sheets

(56) References Cited

U.S. PATENT DOCUMENTS

| | | |
|---|---|---|
| 2011/0230360 A1 | 9/2011 | Stephan et al. |
| 2013/0078667 A1* | 3/2013 | Goodman ............. G01N 21/65 |
| | | 435/34 |

OTHER PUBLICATIONS

Nyga et al. 3D tumor models: novel in vitro approaches to cancer studies, J. Cell Communication. Signal (2011) 5: 239-248.*

Gurski et al. "3D Matrices for Anti-Cancer Drug Testing and Development" Oncology Issues Jan./Feb. 2010.*

Gout, Peter W., and Yuzhuo Wang. "Drug Sensitivity Testing for Personalized Lung Cancer Therapy." National Center for Biotechnology Information. U.S. National Library of Medicine, Feb. 4, 2012.

Hirschhaeuser F, et al. Multicellular tumor spheroids: An underestimated tool is catching up again, Journal of Biotechnology, 2010.

Gurski, LA et al. Hyaluronic Acid-Based Hydrogels as 3D Matrices for in Vitro Evaluation of Chemotherapeutic Drugs Using Poorly Adherent Prostate Cancer Cells. Biomaterials, 2009, 30(3)6076-6085.

Gurski, LA et al. Corrigendum to "Hyaluronic acid-based hydrogels as 3D matrices for in vitro evaluation of chemotherapeutic drugs using poorly adherent prostate cancer cells" [Biomaterials. 30 (2009) 6076-6085]. Biomaterials 2010. 31, pp. 4248.

Elkayam, T et al. Enhancing the Drug Metabolism Activities of C3A—A Human Hepatocyte Cell Line—by Tissue Engineering Within Alginate Scaffolds. Tissue Engineering, 2006, 12(5).

Shin, J-Y et al. Efficient formation of cell spheroids using polymer nanofibers. Biotechnology Letters, Dec. 30, 2011.

Wang D, et al. Thermoreversible Hydrogel for In Situ Generation and Release of HepG2 Spheroids. Biomacromolecules. 2011, 12, pp. 578-584.

Chung TW, et al. Preparation of alginate/galactosylated chitosan scaffold for hepatocyte attachment. Biomaterials 2002, 23 pp. 2827-2834.

Ivascu A and Kubbies M. Diversity of cell-mediated adhesions in breast cancer spheroids. International Journal of Oncology 31: 1403-1413, 2007.

Semino CE, et al. Functional differentiation of hepatocyte-like spheroid structures from putative liver progenitor cells in three-dimensional peptide scaffolds. Differentiation (2003) 71:262-270.

Ho WJ, et al. Incorporation of multicellular spheroids into 3-D polymeric scaffolds provides an improved tumor model for screening anticancer drugs. Cancer Science 2010, 101(12) pp. 2637-2643.

Tsai S-W, et al. MG63 Osteoblast-Like Cells Exhibit Different Behavior when Grown on Electrospun Collagen Matrix versus Electrospun Gelatin Matrix. PLoS One 2012, 7(2), e31200.

Agudelo-Garcia PA, et al. Glioma Cell Migration on Three-dimensional Nanofiber Scaffolds Is Regulated by Substrate Topography and Abolished by Inhibition of STAT3 Signaling. Neoplasia (2011) 13, 831-840.

Johnson J et al. Quantitative Analysis of Complex Glioma Cell Migration on Electrospun Polycaprolactone Using Time-Lapse Microscopy. Tissue Engineering: Part C, vol. 15, No. 4, 2009.

Liang D et al. Functional Electrospun Nanofibrous Scaffolds for Biomedical Applications. Adv Drug Deliv Rev. Dec. 10, 2007; 59(14): 1392-1412.

Luu YK et al. Development of a nanostructured DNA delivery scaffold via electrospinning of PLGA and PLA—PEG block copolymers. Journal of Controlled Release 89 (2003) 341-353.

Zanatta G et al. Viability of Mesenchymal Stem Cells during Electrospinning. Brazilian Journal of Medical and Biological Research. 2012, 45(2) 93-178.

Pampaloni et al. The third dimension bridges the gap between cell culture and live tissue. Nature Reviews Molecular Cell Biology 8, 839-845 (Oct. 2007).

Timmins et al. Method for the generation and cultivation of functional three-dimensional mammary constructs without exogenous extracellular matrix. Cell and Tissue Research, Apr. 2005, vol. 320, Issue 1, pp. 207-210.

Castaneda and Kinne. Short exposure to millimolar concentrations of ethanol induces apoptotic cell death in multicellular HepG2 spheroids. Journal of Cancer Research and Clinical Oncology. May 2000, vol. 126, Issue 6, pp. 305-310.

Horning et al. 3-D Tumor Model for In Vitro Evaluation of Anticancer Drugs. Mol. Pharmaceutics, 2008, 5 (5), pp. 849-862.

Chua et al. Stable immobilization of rat hepatocyte spheroids on galactosylated nanofiber scaffold. Biomaterials, vol. 26, Issue 15, May 2005, pp. 2537-2547.

Tzvetkova-Chevolleau et al. The motility of normal and cancer cells in response to the combined influence of the substrate rigidity and anisotropic microstructure. Biomaterials. Apr. 2008;29(10):1541-51. 2007.12.016. Epub Jan. 11, 2008.

Wang X, et al. Influence of physicochemical properties of laser-modified polystyrene on bovine serum albumin adsorption and rat C6 glioma cell behavior. Journal of Biomedical Materials Research Part A, vol. 78A, Issue 4, pp. 746-754, Sep. 15, 2006.

Zanatta et al. Mesenchymal Stem Cell Adherence on Poly(D, L-Lactide-Co-Glycolide) Nanofibers Scaffold is Integrin-β1 Receptor Dependent. Journal of Biomedical Nanotechnology, vol. 8, No. 2, Apr. 2012, pp. 211-218(8).

Yu, DG et al. Modified coaxial electrospinning for the preparation of high-quality ketoprofen-loaded cellulose acetate nanofibers. Carbohydrate Polymers. Volume 90, Issue 2, Oct. 1, 2012, pp. 1016-1023.

Sundaramurthi et al 2012. Electrospun nanostructured chitosan—poly(vinyl alcohol) scaffolds: a biomimetic extracellular matrix as dermal substitute. Biomed. Mater. 7 045005.

Samavedi et al. 2012. Response of bone marrow stromal cells to graded co-electrospun scaffolds and its implications for engineering the ligament-bone interface. Biomaterials. Nov. 2012;33(31):7727-35.

Meinel et al. 2012. Electrospun matrices for localized drug delivery: Current technologies and selected biomedical applications. European Journal of Pharmaceutics and Biopharmaceutics. vol. 81, Issue 1, May 2012, pp. 1-13.

Xie & Wang 2006. Electrospun Micro- and Nanofibers for Sustained Delivery of Paclitaxel to Treat C6 Glioma in Vitro. Pharmaceutical Research. Aug. 2006, vol. 23, Issue 8, pp. 1817-1826.

Girard, Yvonne, "A Three Dimensional Scaffold for Anticancer Drug Development" (2013). Graduate Theses and Dissertations. http://scholarcommons.usf.edu/etd/4816.

Gurski, LA et al. 3D Matrices for Anti-Cancer Drug Testing and Development. Oncology Issues Jan./Feb. 2010.

Girard YK et al. A 3D Fibrous Scaffold Inducing Tumoroids: A Platform for Anticancer Drug Development. PLOS One. Oct. 2013, vol. 8, Issue 10, e75345.

Fong ELS et al. Modeling Ewing sarcoma tumors in vitro with 3D scaffolds. PNAS, Apr. 16, 2013, vol. 110, No. 16.

Shin JY. Efficient formation of cell spheroids using polymer nanofibers. Biotechnol Lett (2012) 34:795-803.

* cited by examiner

Naked Scaffold

3P Scaffold

THREE-DIMENSIONAL FIBROUS SCAFFOLDS FOR CELL CULTURE

CROSS REFERENCE TO RELATED APPLICATIONS

This application is a continuation-in-part of U.S. patent application Ser. No. 13/775,536, filed on Feb. 25, 2013, which claims priority benefit of U.S. Provisional Patent Application Ser. No. 61/602,337 filed on Feb. 23, 2012 and U.S. Provisional Patent Application Ser. No. 61/723,922 filed on Nov. 8, 2012, and which claims priority benefit of U.S. Provisional Patent Application Ser. No. 61/861,632 filed on Aug. 2, 2013.

STATEMENT REGARDING FEDERALLY SPONSORED RESEARCH OR DEVELOPMENT

This invention was made with government support under R01 CA152005 awarded by the National Institutes of Health and Grant Number N00014-10-1-0854 awarded by the Office of Naval Research. The government has certain rights in the invention.

FIELD OF THE INVENTION

The invention described herein relates to the field of three-dimensional cell culture scaffolds.

SUMMARY

The disclosure encompasses embodiments of a 3D nanofibrous scaffold produced by electrospinning a mixture of poly(lactic-co-glycolic acid) (PLGA) and a block copolymer of polylactic acid (PLA) and mono-methoxypolyethylene glycol (mPEG) designated as 3P. Cancer cells cultured on the 3P scaffold formed tight aggregates, termed tumoroids, similar to in vivo tumors that depend on the topography and net charge of the scaffold. 3P scaffolds induced tumor cells to undergo the epithelial-to-mesenchymal transition (EMT) as demonstrated by up-regulation of vimentin and loss of E-cadherin expression. The 3P-based tumoroids showed higher resistance to anticancer drugs than the same tumor cells grown as monolayers. Inhibition of ERK and PI3K signal pathways prevented EMT conversion and reduced tumoroid formation, diameter and number.

Fine needle aspirates, collected from tumors in mice, when cultured on the 3P scaffolds of the disclosure formed tumoroids, but showed an even greater decrease in sensitivity to anticancer drugs, compared to tumoroids formed by direct seeding. Accordingly, the 3P scaffolds provide an excellent platform for producing tumoroids from tumor cell lines and from biopsies and that the platform can be used to culture patient biopsies, test for anticancer compounds, and thereby allow the tailoring of a personalized cancer treatment.

BACKGROUND OF THE INVENTION

Three dimensional (3D) cultures provide innovative approaches to study processes that contribute to tumorigenesis because they recapitulate cancer cells in their native in vivo environment. The majority of the supporting data that posits the importance of tumorigenesis has been obtained using two dimensional (2D) cell culture systems. Cells in 2D are subjected to unnatural mechanical and geometric constraints that do not represent the three dimensional (3D) milieu of a tumor. The complex interplay between biochemical, and mechanical properties may be undermined or compromised in 2D cultures and may affect many important functions such as gene and protein expression. Considerations on the mechanical, biochemical and physical properties of any 3D system, aim to mimic the native ECM. One of the major advantages is the potential for rapid experimental manipulation achieved by controlling these parameters that can permit development of sophisticated cancer models. Tailored 3D cell culture scaffolds combining relevant platforms with multiple bio-functionalities will allow for the specific induction of signal transduction pathways, the sorting of different cell types, or the control of cancer cell differentiation. Combination of existing 3D systems that impart separate yet important characteristics that preserve structural and functional in vivo-like complexity to the whole will increase the sophistication of these 3D models. Presently, there exist a significant need for more realistic tumor models to study tumorigenesis and the effective screening of anticancer drugs.

The most commonly used 3D model are spheroids that are used for a variety of experimental studies in chemotherapy and radiotherapy and are being pursued in high throughput screening (HTS) programs for drug development, candidate efficacy and safety. Spheroids impart functional and mass transport properties similar to those observed in micrometastases or poorly vascularized regions in solid tumors (Hirschhaeuser et al., (2010) *J. Biotechnol.* 148: 3-15). These features combined with the complexities of cell-cell and cell-matrix interactions, affect the uptake, penetration, distribution and bioactivity of therapeutic drugs. They are simple 3D structures that can be generated from a wide range of cell types, and form due to the tendency of adherent cells to aggregate and are typically created from single or co-culture techniques such as hanging drop, rotating culture or conclave plate methods to name a few (Pampaloni et al., (2007) *Nat. Revs. Mol. Cell Biol.* 8: 839-845; Timmins et al., Cell Tissue Res. 320: 207-210; Castaneda & Kinne (2000) J. Cancer Res. Clinical Oncol. 126: 305-310).

The inherent limitation of this model is that it is entirely cell based and do not represent the mechanical features of the ECM as a whole. To address this issue various substrates or scaffolds derived from biological, natural or synthetic sources have been used to form hydrogels, films, fibers, micromolded structures in microfluidic devices, and microchips in the construction of spheroids. For example, hepatocytes self-assemble to form spheroids on scaffolds made from alginate, hyaluronic acid, peptide scaffolds, and galactosylated meshes (Gurski et al., (2009) *Biomaterials.* 30: 6076; Gurski et al., (2010) *Biomaterials.* 31: 4248; Elkayam et al., (2006) *Tissue Engineering* 12: 1357-1368; Shin et al., (2012) *Biotech. Letts.* 34: 795-803; Wang et al., (2011) *Biomacromolecules* 12: 578-584; Chung et al., (2002) *Biomaterials* 23: 2827-2834; Ivascu & Kubbies (2007) *Int. J. Oncol.* 31: 1403-1413; Horning et al., (2008) *Mol. Pharmaceutics* 5: 849-862; Semino et al., (2003) *Different: Res. Biol. Diversity* 71: 262-270; Chua et al., (2005) *Biomaterials* 26: 2537-2547).

Incorporation of spheroids into synthetic 3D polymeric scaffolds has been used as a model for screening anticancer drugs (Ho et al., (2010) *Cancer Sci.* 101: 2637-2643). These scaffolds provide support for the spheroids thereby mimicking the physical interaction of the tumor with the topographical features of the native ECM, as for example, between the tumor and the basement membrane.

The interaction of mammalian cells with sub cellular topography has proven to be an important signaling modality in controlling cell function via mechanotransductive cues. The tumor microenvironment consisting of tumor cells and corresponding stroma intimately associate with the physical structures of the ECM during all stages of tumorigenesis. Synthetic substrate topography has been shown to influence cell migration, differentiation, and gene expression. For example, SAL/N cancer fibroblasts cultured on micropatterned PDMS and C6 glioma cells cultured on polystyrene periodic structures exhibit differences in morphology, proliferation and migration in response to various topographical cues (Tzvetkova-Chevolleau et al., (2008) *Biomaterials* 29: 1541-1551; Wang et al., (2006) *J. Biomed. Mats. Res. Part A.* 78A: 746-54).

Electrospinning is a versatile technique used to produce polymeric fibrous scaffolds for cell culture applications. It allows for the preparation of unique matrices of aligned or non-woven meshes containing nano to micrometer sized fibers using diverse materials and fabrication techniques (Zanatta et al., (2012) *Brazilian J. Med. Biol. Res.* 45: 125-130; Zanatta et al., (2012) *J. Biomed. Nanotechnol.* 8: 211-218; Yu et al., (2012) *Carbohydrate Polymers* 90: 1016-1023; Tsai et al., (2012) *PloS one.* 7: e31200; Sundaramurthi et al., (2012) *Biomedical Materials* 7: 045005; Samavedi et al., (2012) *Biomaterials*; Meinel et al., (2012) *Eur. J. Pharmaceut. Biopharmaceutics.* 81: 1-13). Studies have shown that modified electrospun scaffolds simulate favorable functional responses in cancer cells (Agudelo-Garcia et al., (2011) *Neoplasia* 13: 831-896; Johnson et al., (2009) *Tissue Engineering Part C-Methods* 15: 531-540; Xie & Wang (2006) *Pharmaceut. Res.* 23: 1817-1826).

BRIEF DESCRIPTION OF THE DRAWINGS

FIG. 6A shows the dose dependent cytotoxic response of MCF-7 cells to inhibitor doxorubicin.

FIG. 6B shows the dose dependent cytotoxic response of MCF-7 cells to inhibitor LY 294002.

FIG. 6C shows the dose dependent cytotoxic response of MCF-7 cells to inhibitor U0126.

FIG. 7A shows the comparison of EMT gene expression associated with 3D (open bars) vs. 2D (solid bars) culture with a selected group of genes that showed a greater than one-fold difference in differentiation and development.

FIG. 7B shows the comparison of EMT gene expression associated with 3D (open bars) vs. 2D (solid bars) culture with a selected group of genes that showed a greater than one-fold difference in cell growth and proliferation.

FIG. 8A shows the comparison of EMT gene expression associated with 3D (open bars) vs. 2D (solid bars) culture with a selected group of genes that showed a greater than one-fold difference in extracellular matrix and cell adhesion.

FIG. 8B shows the comparison of EMT gene expression associated with 3D (open bars) vs. 2D (solid bars) culture with a selected group of genes that showed a greater than one-fold difference in signaling pathways.

FIG. 13 illustrates the culturing tumor biopsies on 3P scaffold. FNA of implanted LLC1 mouse tumors were cultured on 3P scaffolds for the indicated time. D1, D3, and D5 are "Day 1," "Day 3," and "Day 5," respectively. Cells were stained with calcein AM/EthD-1.

FIG. 14 illustrates the average size of biopsy tumoroids on 3P scaffolds from day 2 to day 5.

FIG. 15 illustrates biopsy tumoroids fixed and immunostained for E-cadherin, vimentin and DAPI.

FIG. 16 illustrates LLC-1 tumoroids and biopsy tumoroids dual-immunostained for CEA and either CD31, F4/80 or SMA and DAPI.

FIG. 17 illustrates biopsy tumoroids (day 2) treated with 1 μM each of LY294002 or U0126 for 3 days. The average size of biopsy tumoroids on 3P scaffolds (n=10 controls, 55 LY294002 and 50 U0126) is shown.

DETAILED DESCRIPTION OF THE INVENTION

Figure 1:
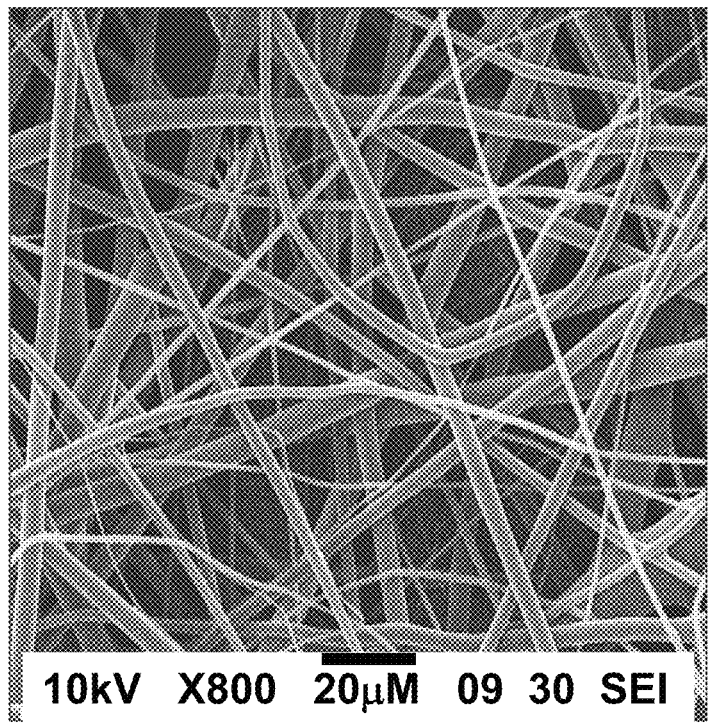
FIG. 1 shows a scanning electron micrograph (SEM) of naked unmodified scaffold and 3P scaffold. Scaffolds consist of fibers arranged as randomly aligned mats.
Figure 1:
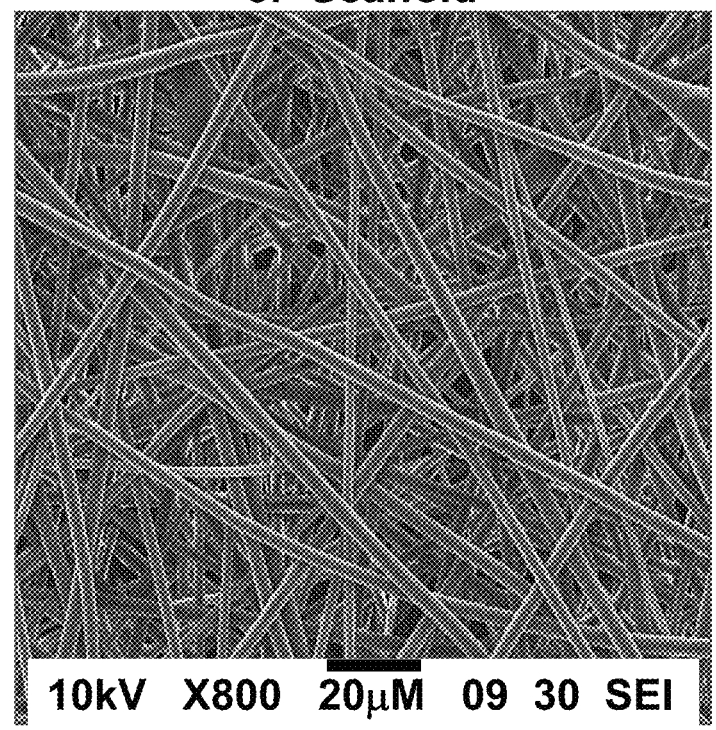

Provided herein is a three-dimensional scaffold composition comprising randomly oriented fibers, wherein the fibers each comprise a polyethylene glycol-polylactic acid block copolymer (PEG-PLA) and a poly(lactic-co-glycolic acid) (PLGA). Also provided are methods for using the three-dimensional scaffolds described herein. Term definitions used in the specification and claims are as follows:

Definitions

As used in the specification and claims, the singular forms "a," "an" and "the" include plural references unless the context clearly dictates otherwise. For example, the term "a cell" includes a plurality of cells, including mixtures thereof.

The term "active derivative" and the like means a modified PEG-PLA or PLGA composition that retains an ability to form a three-dimensional scaffold composition that can be used to grow cancer cell spheroids. Assays for testing the ability of an active derivative to perform in this fashion are provided herein.

When referring to a subject or patient, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intraperitoneal, intra-synovial, intrasternal, intrathecal, intrahepatic, intralesional, and intracranial injections or infusion techniques.

As used herein, the terms "cancer," "cancer cells," "neoplastic cells," "neoplasia," "tumor," and "tumor cells" (used interchangeably) refer to cells which exhibit relatively autonomous growth so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor. In some embodiments, the cancer is prostate cancer.

As used herein, a "cancer cell spheroid" refers to an aggregate of cancer cells.

The terms "cell," "cell line," and "cell culture" include progeny. It is also understood that all progeny may not be precisely identical in DNA content due to deliberate or inadvertent mutations. Variant progeny that have the same function or biological property, as screened for in the originally transformed cell, are included. The "host cells" used in the present invention generally are prokaryotic or eukaryotic hosts.

The term "chitosan" refers to a linear polysaccharide composed of randomly distributed β-(1-4)-linked D-glucosamine (deacetylated unit) and N-acetyl-D-glucosamine (acetylated unit). On average, the molecular weight of commercially produced chitosan is between 3,800 and 20,000 Daltons. In some embodiments, the chitosan has a molecular weight of approximately 3-12 kDa. In one embodiment the chitosan is water soluble and has a molecular weight of approximately 10 kDa.

It should be understood that the term "coating" does not require a complete coverage of the coated object and that partial coverage is encompassed by the term.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "effective amount" is an amount sufficient to effect beneficial or desired results. An effective amount can be administered in one or more administrations, applications, or dosages.

The term "fibrous scaffold" refers herein to a three dimensional structure formed by randomly oriented fibers. In some embodiments, electrospining methods are used to achieve the randomly oriented fiber construction.

The term "isolated" means separated from constituents, cellular and otherwise, in which the polynucleotide, peptide, polypeptide, protein, antibody, or fragments thereof are normally associated with in nature. In one aspect of this invention, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, or antibody, or fragments thereof, does not require "isolation" to distinguish it from its naturally occurring counterpart. In addition, a "concentrated," "separated," or "diluted" polynucleotide, peptide, polypeptide, protein, or antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, or antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

"Mammal" for purposes of treatment refers to any animal classified as a mammal, including human, domestic and farm animals, nonhuman primates, and zoo, sports, or pet animals, such as dogs, horses, cats, cows, etc.

The term "particulate" refers to powders, granular substances, and the like.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier or excipient" means a carrier or excipient that is useful in preparing a pharmaceutical composition that is generally safe, non-toxic and neither biologically nor otherwise undesirable and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, emulsions, such as an oil/water or water/oil emulsion, and various types of wetting agents. The compositions also can include stabilizers and preservatives.

The term "pharmaceutically acceptable salts" refers to any acid or base addition salt whose counter-ions are non-toxic to the subject to which they are administered in pharmaceutical doses of the salts.

The terms "pharmaceutically effective amount," "therapeutically effective amount," or "therapeutically effective dose" refer to the amount of a compound that will elicit the biological or medical response of a tissue, system, animal, or human that is being sought by the researcher, veterinarian, medical doctor or other clinician.

The term "PLGA" refers to poly(lactic-co-glycolic acid) that is synthesized by means of random ring-opening co-polymerization of two different monomers, the cyclic dimers (1,4-dioxane-2,5-diones) of glycolic acid and lactic acid. Depending on the ratio of lactide to glycolide used for the polymerization, different forms of PLGA can be obtained: these are usually identified in regard to the monomers' ratio used (e.g. PLGA 75:25 identifies a copolymer whose composition is 75% lactic acid and 25% glycolic acid).

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool.

A "subject," "individual," or "patient," used interchangeably herein, refers to a vertebrate, preferably a mammal, more preferably a human. Mammals include, but are not limited to, murines, simians, humans, farm animals, sport animals, and pets.

The term "therapeutically effective amount" includes that amount of a compound that, when administered, is sufficient to prevent development of, or alleviate to some extent one or more of the symptoms of, the condition or disorder being treated. The therapeutically effective amount will vary depending on the compound, the disorder or conditions and their severity, the route of administration, time of administration, rate of excretion, drug combination, judgment of the treating physician, dosage form, and the age, weight, general health, sex and/or diet of the subject to be treated.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

Using these terms and definitions, provided herein is a three-dimensional scaffold composition comprising randomly oriented fibers, wherein the fibers comprise a polyethylene glycol-polylactic acid block copolymer (PEG-PLA) and a poly(lactic-co-glycolic acid) (PLGA).

The chemical structure of PEG is H—(O—CH$_2$—CH$_2$)$_n$—OH. PEG is also known as polyethylene oxide (PEO) or polyoxyethylene (POE), depending on its molecular weight. PEG usually refers to oligomers and polymers with a molecular mass below 20,000 g/mol. PEGs are prepared by polymerization of ethylene oxide and are commercially available over a wide range of molecular weights from 300 g/mol to 10,000,000 g/mol. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete. In some embodiments, the PEG used to prepare the 3P and 3PC scaffolds described herein is a monomethoxy glycol (mPEG) having a molecular weight between approximately 0.5 and 20 kDa. Included herein are embodiments wherein the molecular weight of the PEG or mPEG is approximately 0.5, 1, 2, 3, 4, 5, 6, 7, 8, 9, 10, 11, 12, 13, 14, 15, 16, 17, 18, 19, or 20 kDa. In one embodiment, the molecular weight of PEG is approximately 2 kDa.

Polylactic acid or polylactide (PLA) ((C$_3$H$_4$O$_2$)$_n$) is a thermoplastic aliphatic polyester derived from renewable resources, such as corn starch, tapioca roots, chips or starch, or sugarcane. Polymerization of a racemic mixture of L- and D-lactides usually leads to the synthesis of poly-DL-lactide (PDLLA), which is amorphous. Use of stereospecific catalysts can lead to heterotactic PLA which has been found to show crystallinity. The degree of crystallinity, and hence many important properties, is largely controlled by the ratio of D to L enantiomers used, and to a lesser extent on the type of catalyst used. Due to the chiral nature of lactic acid, several distinct forms of polylactide exist: poly-L-lactide (PLLA) is the product resulting from polymerization of L,L-lactide (also known as L-lactide). PLLA has a crystallinity of around 37%, a glass transition temperature between 60-65° C., a melting temperature between 173-178° C. and a tensile modulus between 2.7-16 Gpa. Accordingly, the 3P and 3PC scaffolds provided herein can comprise a PLA composition having only D-enantiomers, only L-enantiomers or a mixture of D- and L-enantiomers. In some embodiments, the PLA composition used to prepare the 3P or 3PC composition contains a racemic mixture of D- and L-enantiomers.

PLGA is synthesized by means of random ring-opening co-polymerization of two different monomers, the cyclic dimers (1,4-dioxane-2,5-diones) of glycolic acid and lactic acid. Common catalysts used in the preparation of this polymer include tin(II) 2-ethylhexanoate, tin(II) alkoxides, or aluminum isopropoxide. During polymerization, successive monomeric units (of glycolic or lactic acid) are linked together in PLGA by ester linkages, thus yielding a linear, aliphatic polyester as a product. Depending on the ratio of lactide to glycolide used for the polymerization, different forms of PLGA can be obtained: these are usually identified in regard to the monomers' ratio used (e.g. PLGA 75:25 identifies a copolymer whose composition is 75% lactic acid and 25% glycolic acid). In one embodiment, the PLGA contains approximately 85% lactic acid and 15% glycolic acid. Also included herein are embodiments, where the lactic acid:glycolic ratio of PLGA is approximately 75:25, 80:20, 85:15, 90:10, and 95:5.

In some embodiments, the 3P scaffold is composed predominantly of poly(lactide-co-glycolide) (PLGA) random copolymer and a poly-lactide-poly(ethylene glycol) (PLA-PEG) block copolymer. In certain further embodiments, the 3P scaffold also comprises chitosan. The chitosan can be coated onto the 3P scaffold. Chitosan coated scaffolds are referred to herein as 3PC scaffolds. The fiber polymer can be constructed by open ring polymerization of mPEG and PLA mixed with PLGA and electrospun. Both PLGA and PLA are used extensively in electrospinning for tissue engineering and drug delivery applications because they possess good mechanical properties, controlled degradability, and excellent biocompatibility [Zhou H, et al., Fabrication aspects of PLA-CaP/PLGA-CaP composites for orthopedic applications: A review. Acta biomaterialia. 2012; 8:1999-2016; Xin X J, et al., Continuing differentiation of human mesenchymal stem cells and induced chondrogenic and osteogenic lineages in electrospun PLGA nanofiber scaffold. Biomaterials. 2007; 28:316-25; Kim K, et al. Incorporation and controlled release of a hydrophilic antibiotic using poly (lactide-co-glycolide)-based electrospun nanofibrous scaffolds. Journal of Controlled Release. 2004; 98:47-56.] PEG is used to modify and enhance the hydrophilicity of the fibers; in addition it is nontoxic and non-immunogenic. PEG's protein-resistant properties arise from imparted nonionic charges, and a high excluded volume which facilitate steric repulsion thus minimizing the adsorption of proteins. Typical methods for spheroid formation employ similar non adherent surface modifications.

In some embodiments, the ratio of PEG-PLA to PLGA in each scaffold fiber is approximately 1:4. In other embodiments, the ratio of PEG-PLA to PLGA in each scaffold fiber is approximately 1:10. In still other embodiments, the ratio of PEG-PLA to PLGA in each scaffold fiber is approximately 1:2, 1:3, 1:4, 1:5, 1:6, 1:7, 1:8, 1:9, 1:10 or 1:20.

The PEG-PLA and PLGA can be formed into fibers via any method known to those of skill in the art. In some embodiments, solutions of PEG-PLA and PLGA are electrospun to form PEG-PLA-PLGA fibers. The scaffold fibers can be electrospun at any voltage, flow rate, and distance that provide for a fiber diameter between approximately 0.3 and 10 µm, or more preferably a fiber diameter between approximately 0.69 to 4.18 µm. In one embodiment, solutions of PEG-PLA and PLGA are electrospun at a positive voltage of 16 kV at a flow rate of 0.2 ml/hour and a distance of 13 cm using a high voltage power supply. The fibers were collected onto an aluminum covered copper plate at a fixed distance of approximately 70 mm. The present invention further includes a 3P or 3PC scaffold prepared by collecting the electrospun fibers at a fixed distance between approximately 60 mm and 80 mm.

The resulting 3P or 3PC scaffold is a three-dimensional fibrous scaffold having pores. In some embodiments, the scaffold comprises pores having a diameter of less than approximately 20 µm. In other embodiments, the 3P or 3PC scaffold comprises pores having a diameter of less than approximately 15, 10 or 5 µm.

It is a surprising finding of the present invention that cancer cells grown on the 3P scaffold form spheroids. The examples below demonstrate an analysis of the effect of the 3P scaffold on cell proliferation, spheroid formation and therapeutic drug efficacy. Using different cancer cell lines it was determined that spheroid formation on the scaffold induced epithelial mesenchymal transition (EMT) an embryonic program that reemerges during cancer metastasis. Signal transduction of EMT conversion was examined by the use of pathway specific inhibitors and demonstrated that these pathways were involved in spheroid formation and EMT induction on the scaffold. Gene expression analysis elucidated the molecular mechanisms and signaling pathways involved in the transition and identified key genes associated with this process. The ability of the scaffold to monitor pharmacological efficacy was also analyzed by using known anti-tumor agents as control modulators of EMT to abrogate growth and differentiation of cancer cells. Accordingly, the examples demonstrate that the 3P scaffolds described herein can be utilized as a platform to study processes in tumorigenesis and can be used to evaluate anti-cancer therapies as an intermediate decision-making step in high throughput screening of drugs to treat cancer.

Accordingly, provided herein are methods for screening pharmaceuticals for cancer treatment efficacy using the 3P scaffolds. In these methods, the 3P scaffolds are seeded with cancer cells, spheroids are allowed to form, and pharmaceuticals are administered to the cells in the scaffold for a given period of time. Dead and live cancer cells are then quantitated and the efficacy of the pharmaceutical for cancer treatment is determined. Also provided herein are methods for growing cancer cell spheroids, methods for tissue culture, methods for tissue regeneration, methods for treating arthritis, and methods for wound therapy.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. All patents, patent applications, and publications referenced herein are incorporated by reference in their entirety for all purposes.

EXAMPLES

Example 1

Preparation and Characterization of the 3P and 3PC scaffolds: The 3P scaffold was constructed by electrospinning the co-block polymer mPEG/LA and PLGA dissolved in appropriate organic solvents. A PLGA unmodified scaffold was also constructed to compare the effects of the 3D environment. More specifically, methoxy PEG-PLA was prepared by ring-opening polymerization. Briefly, 3,6-Dimethyl-1,4-dioxane-2,5-dione (LA) (Fisher) was dried in a vacuum oven at 40° C. overnight. One gram mono-methoxy poly(ethylene glycol) (mPEG) (MW 2000, Sigma) was added into a 100 mL dried three-necked round-bottom flask and stirred at 80° C. for 2 hours under vacuum. Four grams or 10 grams of dry LA monomer (to make the 3P 1:4 and 3P 1:10 scaffolds respectively) and 0.2 wt % stannous octoate (Sn(Oct)2) (Sigma) were added to the flask under the protection of argon gas. The mixture was dissolved in 20 ml anhydrous toluene and heated at 140° C. under argon gas for 5 hours. Solid products of the diblock copolymers were obtained by addition of the polymer solution to ice cold diethyl ether. The products were dissolved in dichloromethane and precipitated in cold diethyl ether twice, for purification. The final copolymer was dried in a vacuum oven at 50° C. for 48 hours.

Poly(lactic co glycolic acid) (MW 50-70 kDa, 85:15, Sigma) and the mPEG-PLA polymer described above were then dissolved in a solution of dichloromethane and chloroform (80/20 v/v). Briefly, 1.2 grams of PLGA and 0.3 grams of mPEG-PLA were used to construct the 3P scaffold. The solutions were electrospun at a positive voltage of 16 kV at a flow rate of 0.2 ml/hour and a distance of 13 cm using a high voltage power supply (Gamma High Voltage research, USA). The fibers were collected onto an aluminium covered copper plate at a fixed distance of 70 mm.

In some embodiments, both mPEG and PLA were placed under vacuum and dried (mPEG was dried at 800 C and PLA at 500° C.). Temperatures were maintained for at least 1 hour to remove all moisture. To make the 1:10 (PEG:PLA) concentration, add 0.5 mPEG and 5 grams of PLA to 20 ml of Toluene and 10 ul of TEH. For the 1:4, 1 gram of mPEG and 4 grams PLA were used. The mixture was stirred under argon at 140° C. for 5 hours at room temperature. The solution was allowed to cool to room temperature overnight. The mPEG/PLA copolymer was precipitated using 60 ml of diethyl ether that was cooled on ice. The mPEG/PLA solution was added to the cold diethyl ether drop wise. The solution turned from clear to cloudy. The solution was then stirred on ice for 2.5 hours. The sticky precipitate that formed at the bottom of the flask was then removed and dissolved in 10 ml chloroform, then precipitated in ether. This was repeated twice. The product was collected in a glass vial and left to dry for at least two days in a vacuum oven at 50° C. 1.375 grams of PLGA and 0.075 grams of the 1:10 mPEG-PLA polymer was added to 5 ml of a solution of dichloromethane and chloroform (80:20 v/v). 0.3 gms of PLGA and 1.2 grams of the 1:4 mPEG-PLA polymer was added to 5 ml of a solution of dichloromethane and chloroform (80:20 v/v). The solutions were allowed to repolymerize for 3 days then electrospun at a positive voltage of 14 KV at a flow rate of 0.2 ml/hr.

In some embodiments, the 3P scaffold was deep coated with chitosan (90% deacylation). More specifically, the 3P scaffolds were cut into 8 $mm^2$ squares and sterilized by UV. The 3P scaffolds were then deep coated by soaking overnight in 0.1% Chitosan in 0.5% acetic acid solution. The scaffolds were washed in PBS three times prior being used for cell cultures. These chitosan-coated scaffolds are referred to herein as 3PC, CMN or CFMN scaffolds. Each of these designations refers to the 3PC scaffold.

The scaffolds provided good spatial interconnectivity between cells, a high surface to volume ratio and good porocity for fluid transport. The parameters that affect the pore size, diameter and thickness of the scaffold included voltage, needle collection distance and concentration of the polymer in the solvent. Scanning electron microscopy (SEM) of the 3P scaffold showed randomly aligned fibers that combine to form a highly porous mesh (FIG. 1). The diameter of the fibers ranged from 0.69 to 4.18 μm and naked scaffold range from 0.61 to 4.95 um with pores of mainly subcellular sizes (<10 um).

Figure 2A:
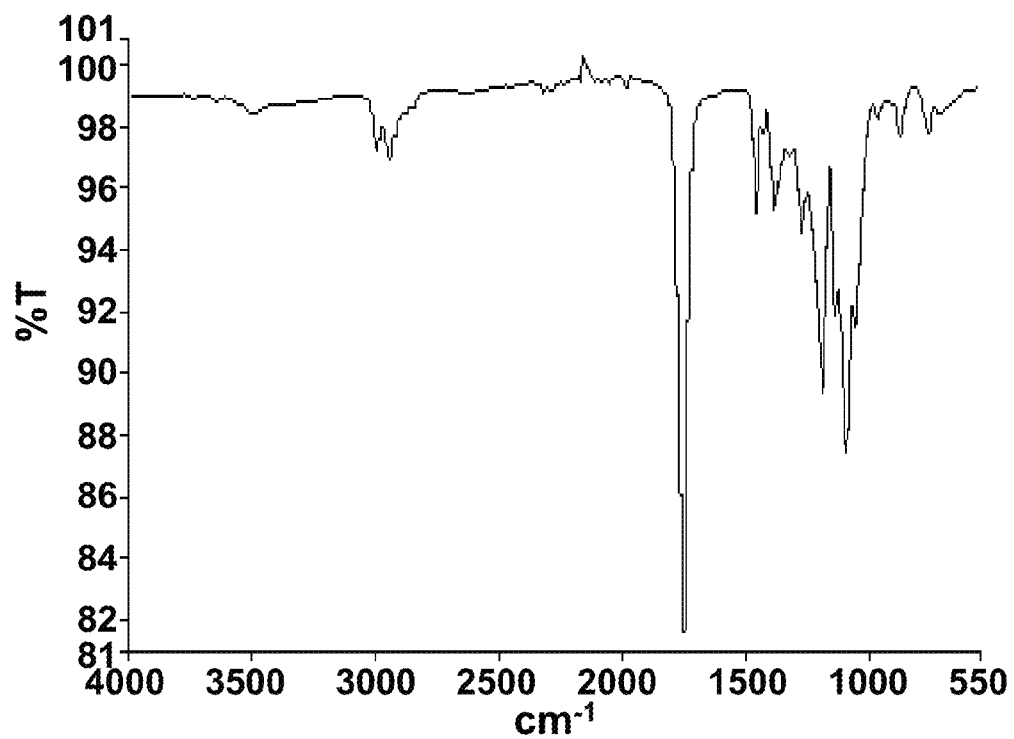
FIG. 2A shows an FTIR of the 3P scaffold. The peak at 1760 cm$^{-1}$ can be assigned to the carbonyl group of PLA 1087 and the peak at 1184 cm$^{-1}$ can be assigned to the —C—O—C bond of mPEG, PLA and PLGA.

FTIR of the 3P scaffold showed strong absorption at 1760 $cm^{-1}$ assigned to —C═O stretch of mPEG, PLA and PLGA respectively. The stretch of the C—O—C band is shown at 1087 and 1184 $cm^{-1}$. The peaks at 2850 and 2950 represent —$CH_2$ stretching (FIG. 2A). The FTIR of mPEG/PLA and PLGA have similar characteristic peaks since they basically have the same functional groups. The molecular weight of the di-block copolymer was determined by $^1H$ nuclear magnetic resonance spectroscopy using the intensity of the terminal methoxy proton signal of LA at Q 3.39 ppm. The weight ratio of the repeated PEG-LA units was calculated to be 7.08 from the integral values of characteristic peaks, and the molecular weight was determined to be 23,100 Da.

Figure 2B:
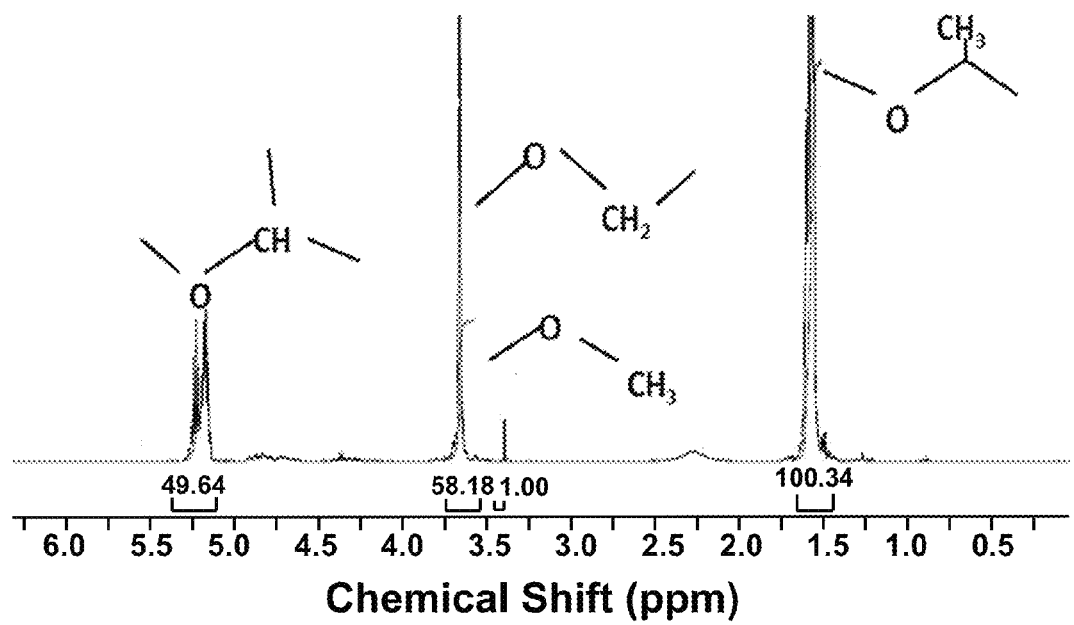
FIG. 2B shows a $^1$H NMR of the 3P scaffold which confirms that PLA was copolymerized with mPEG. The integral of the signal at 3.3 ppm is attributed to the three equivalent hydrogen atoms of the methyl group on mPEG-OH and used as the internal standard. The molecular weight of the PLA block is 23.1 kDa.

The molecular weight of the diblock copolymer was determined by 1H nuclear magnetic resonance spectroscopy using the intensity of the terminal methoxy proton signal of mPEG at Q 3.39 ppm. The weight ratio of the repeated PEG-LA units was calculated to be from the integral values of characteristic peaks. The 1H NMR confirmed that PLA was copolymerized with mPEG as shown in FIG. 2B.

Figure 3:
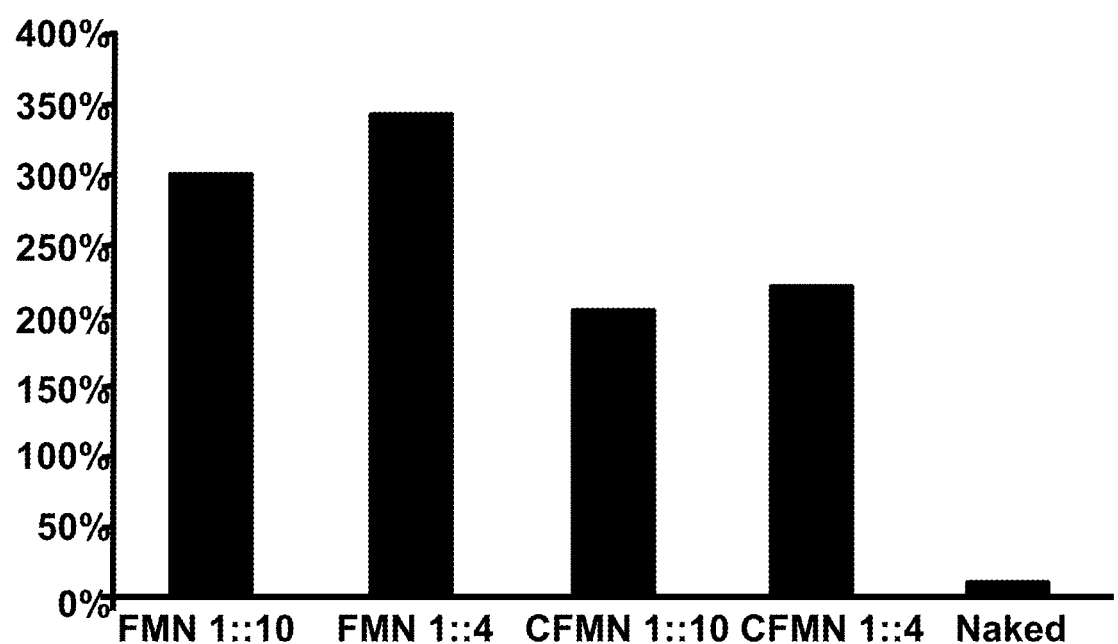
FIG. 3 shows the swelling volume ratio (SWR) of FMN (3P), CFMN (3PC), and naked scaffolds as measured after the scaffolds were immersed in water for 24 hours and were considered to have reached the equilibrium of water uptake. The SWR indicates the hydrophilic potential of the scaffolds.

The swelling volume ratio (SWR) of MN (3P), CMN (3PC) and naked scaffolds was measured after the scaffolds were immersed in water for 24 hours and was considered to reach the equilibrium of water uptake. The SWR indicates the hydrophilic potential of the scaffolds. The results are shown in FIG. 3.

Example 2

Formation and growth of spheroids on 3P scaffolds: All of MCF-7, MDA-MB, MCF-10A breast cancer, PC3 prostate cancer, B16 melanoma, BG-1 ovarian and LLC Lewis lung cancer cells, grew spheroids on the 3P scaffolds. In one experiment, LLC cells ($5\times10^3$) were cultured on monolayer, naked and 3P scaffolds from day 1 to day 5. Cells on monolayer and naked scaffolds did not form spheroids, but cells on 3P scaffolds formed spheroids beginning at day 3 and progressively increased in size at day 5. Cells were stained with calceinAM/EthD-1 for live (green) and dead (red) cells to demonstrate multiple spheroids of live cells on the 3P scaffolds (data not shown).

SEM analysis of the cells grown on the 3P scaffolds showed initial intertwining of the fibers into and around the spheroids that allowed for anchoring and stabilization (data not shown). Scanning electron microscopy of spheroids was performed as follows. LLC spheroids (cell count $5 \times 10^3$) were cultured on the scaffolds for 3 days. The scaffolds were fixed in a 50:50 (v/v) solution of 2.5% glutaraldehyde in 0.2 M cocadalate buffer (pH 7.1) for 24 hours. The scaffolds were washed in buffer then dehydration in 1% osmium tetroxide in cocadylate buffer at 40° C. for one hour. The scaffolds were washed in cocadalate buffer then further dehydrated in an ascending series of ethanol at concentrations 10%, 35%, 50%, 70%, 95% and 100% for ten minutes. Final dehydration was done in hexamethyldisilazane (HMDS) for 10 minutes. Samples were air dried then sputter coated with gold at a density of 19.32/cm3 for 30 seconds under argon gas. SEM of the scaffold was viewed on a Jeol JSM 6490 scanning electron microscope. To calculate the diameters of the spheroids, the entire scaffold was scanned for full planar images. All spheroids were measured for diameter using Image J software.

Analysis of MCF-7 spheroids in particular revealed a smooth surface, tight cell junction and indistinguishable cellular boundaries. The spheroids appeared flattened on the surface with intertwining fibers that form a spheroid/fiber composite. Notably, cells proliferated on unmodified PLGA scaffold and monolayer but did not form spheroids.

Figure 4A:
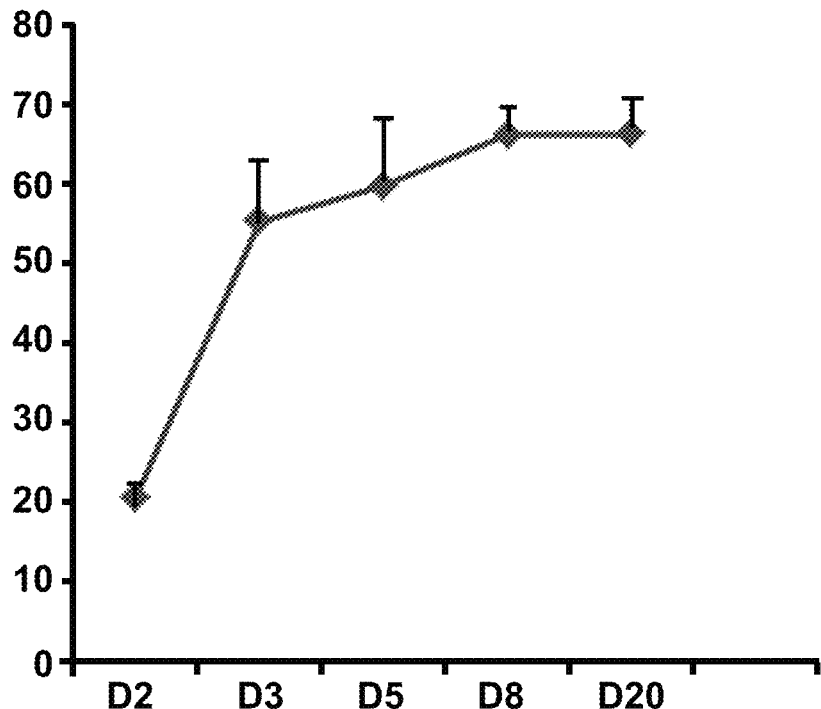
FIG. 4A is a graph showing the average size of LLC spheroids grown on the 3P scaffold (n=10) from day 2 to day 20. Spheroids that were placed in 96 well plates grew on 3P scaffolds of average size 5 mm$^2$. Confocal images of a 20 day spheroid showed the inner necrotic core surrounded by a tight layer of proliferating cells.
Figure 4B:
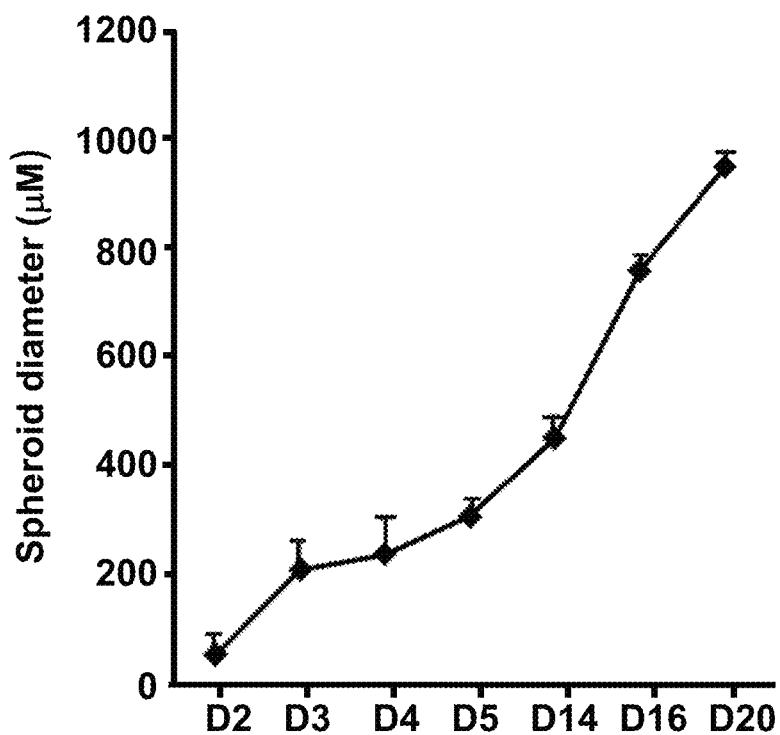
FIG. 4B is a graph showing the average number of spheroids per scaffold. Spheroids that were placed in 96 well plates grew on 3P scaffolds of average size 5 mm$^2$. Confocal images of a 20 day spheroid showed the inner necrotic core surrounded by a tight layer of proliferating cells.

FIG. 4 shows the average size of LLC spheroids on 3P scaffold (n=10) from day 2 to day 20 (FIG. 4A) and the average number of spheroids per scaffold (FIG. 4B). Spheroids that grew on 3P scaffolds had an average size 5 mm² that were placed in 96 well plates. A confocal image of a 20 day spheroid showed the inner necrotic core surrounded by a tight layer of proliferating cells (data not shown). The parameters essential for spheroid formation depended on cell type, concentration and time from initial seeding of the cells. It was observed that the higher the concentrations of cells, the faster the spheroids were formed with subsequent increase in diameter and numbers over time and this was observed for all cell types (FIG. 4). SEM of the spheroids indicated tight aggregates of cells with cellular boundaries that were indistinguishable at the periphery.

Focusing on LLC cells, it was observed that cells cultured on the 3P scaffold formed spheroids of variable sizes. At $5 \times 10^3$ from day 2 to day 20, the average size were 48.3+/−7.8 μm to 945.44 μm+/−28.8, respectively and the average spheroid number went from 20.49+/−2.01 to 52.76+/−3.86 (data not shown). The spheroids could be easily detached and transferred to new wells or scaffolds for long term culture.

Typically, tumor spheroids exhibit a spherical proliferative geometry defined by inward and outward diffusion gradients. Beyond the diffusion capacity of oxygen and fresh growth media, the innermost cells become quiescent and die from apoptosis or necrosis. Such results were observed in day 20 spheroids that had attained diameters above 500 μm. The viability of the cells within the spheroids was assessed using calcein AM/EthD-1 live/dead assay that stain dead cells red and live cells green, and this assay demonstrated that cells on the periphery appeared to encompass an inner core of dead cells (data not shown).

Example 3

A unique combination of topography and chemistry allows spheroid formation: To explore the effects of topography and chemistry on spheroid formation, LLC cells were cultured on PLGA, PLA and PLGA/PEG, PLA/PEG, and PLGA/PLA/PEG coated glass coverslips. It was observed that cells proliferated on all of the substrates but only self-assembled to spheroids on the PLGA/PLA/PEG coverslips. These spheroids however were fewer and easily dissociated when the substrate separated from the coverslip in day 3. Cells on the PLA/PEG construct grew large disorganized aggregates of cells that lacked the defined shape and structure observed in the 3P spheroids.

To further elucidate the effects of surface chemistry on spheroid formation, the composite 3P/Chitosan scaffold was constructed as described above (referred to herein as the 3PC or CMN scaffold). It was observed that cells proliferated but did not form spheroids (data not shown). Chitosan was used because it is a naturally occurring polysaccharide that imparts a positive charge at physiological pH and increases hydrophilic properties of the scaffold.

Formation and maintenance of spheroids on the 3P scaffolds support the observation that spheroid formation was directed by topographical and chemical cues transferred dynamically between the 3P ECM-like scaffold and the cells. It was observed that spheroids transferred to a regular tissue culture plate (TCP) coated for monolayer culture, adhered to the plate and grew out from the spheroid. LLC cells gradually migrated away from the spheroid from day 1 to day 4 at 0, 0.67+/−0.1, 1.4+/−0.14, 2.1+/−0.29 mm, respectively, and ultimately formed a confluent monolayer (data not shown). Spheroids transferred to new scaffolds maintained their morphology and shape over the same time period. In addition to topography and chemistry, other cues present in the 2D environment but absent in the 3P scaffold, may play a role in instigating outward migration on the TCP, for example, factors such as substrate density and elasticity, difference in cell polarity and pressure gradients within the spheroids reacting to unnatural constraints exerted by the 2D environment.

Example 4

Spheroid formation induces EMT signaling: Based on the finding that the 3P scaffold induced tumor cells to form multicellular spheroids that resemble the micrometastasis of avascular tumors, whether spheroid formation on the scaffolds induced EMT in LLC lung cancer cell line was examined. The results were then compared with cells grown on PLGA scaffold and in monolayer culture. At the molecular level, the epithelial-mesenchymal transition (EMT) is defined by the loss of the cell-cell adhesion molecules E-cadherin and the transcriptional induction of mesenchymal marker vimentin.

To perform these studies, LLC spheroids were cultured for 4 days (seeding density $5 \times 10^3$). Spheroids were fixed with 4% paraformaldehyde for 20 minutes, permeabilized with 0.1% Triton X-100 for 20 minutes at 25° C., and blocked using 3% BSA. Cells were incubated overnight with vimentin or E-cadherin Anatibody followed by Alexa Fluor 555 or 488 cojugated anti-mouse secondary Ab and Dapi. Cells were viewed using an Olympus BX51 microscope.

Figure 5A:
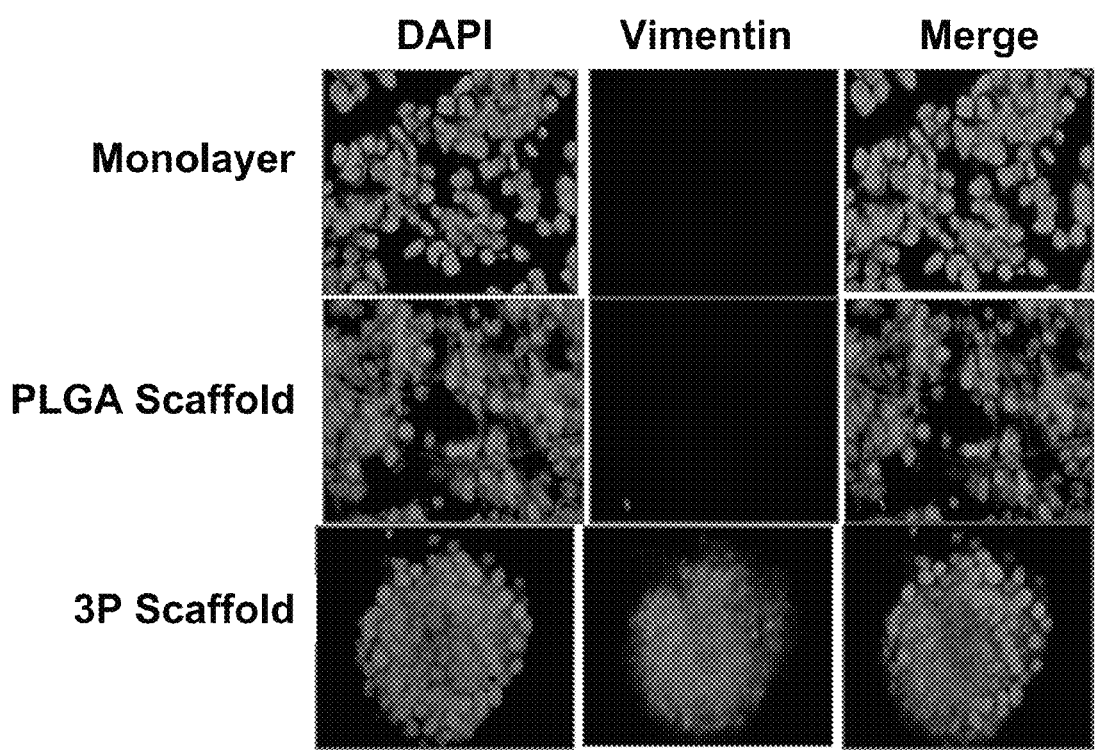
FIGS. 5A and 5B show that the 3P scaffold induces spheroid formation and EMT. The figures shows fluorescent images of LLC cells cultured on monolayer, PLGA, and 3P scaffolds immunostained with E-cadherin and vimentin antibodies and Dapi. Cells were cultured for three days then stained for markers. Spheroids stained positive for the mesynchymal marker vimentin and negative for the epithelial marker E-cadherin while cells on the monolayer and PLGA scaffold maintained epithelial marker expressions.
Figure 5B:
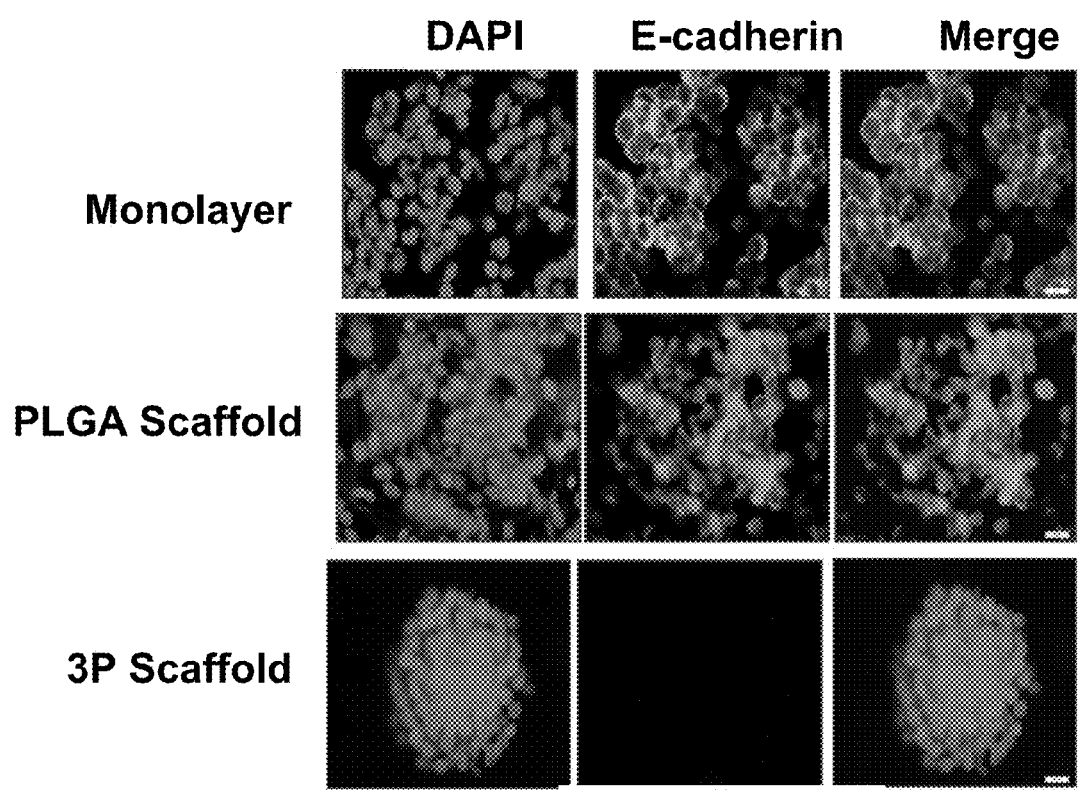

As shown in FIG. 5A, spheroids grown on the scaffold at day 3 showed expression of vimentin while no vimentin expression was observed in the monolayer culture or on cells cultured on PLGA scaffold. Additionally, spheroids exhibited a loss of E-Cadherin expression on the 3P scaffold, while cells cultured on monolayer and PLGA scaffold retain this expression (FIG. 5B). This suggests that spheroid formation correlates with enhanced invasive potential and tumorgenicity, characteristics that define EMT and that appears to be manifested within the context of the 3P environment. To determine the timeline of EMT induction, LLC cells were cultured on the 3P scaffold and stained for vimentin and E-cadherin from day 1 to day 4 culture. It was observed that the onset of EMT occurred at day 3 and continued into day 4 correlating with the self-assembly of the cells into spheroids (data not shown).

Example 5

Pharmacological intervention abrogates spheroid formation and disrupts EMT signaling: To examine the effects of known anti-tumor agents as control modulators of EMT, MCF-7 and LLC cells were treated with phosphotidyl inositol-3 kinase (PI3K) pathway inhibitor Ly294002 and the mitogen activated protein kinase (MAPK) pathway inhibitor U0126. To determine if spheroid formation can be inhibited by these drugs, MCF-7 cells were treated after 24 hours of culture on the 3P scaffolds with Ly294002 and U0126 and observed for spheroid formation on day 4. All anti-tumor agents prevented spheroid formation and proliferation on 3P scaffolds (data not shown). In addition, these compounds were efficient at down regulating vimentin while maintaining E-cadherin expression in cells similar to that observed with cells cultured on PLGA scaffold alone and on the monolayer. To determine if treatment by these agents would deregulate EMT in fully formed spheroids, the same concentration of drugs were administered to LLC spheroids cultured at day 4. A lack of vimentin expression and a concomitant expression of E-cadherin was again observed suggesting EMT inhibition. As expected, untreated spheroids were positive for EMT marker expression. These findings implicate both PI3K and the MAPK signaling as significant pathways that contribute to cytoskeletal rearrangement and cell-cell adhesion, properties necessary for spheroid formation and EMT expression on the 3P scaffold.

Example 6

Drug efficacy analysis using 3P scaffold: To assess the ability of the 3P scaffold to monitor therapeutic efficacy to treat tumors, LLC spheroids were treated with different concentrations of the PI3K pathway inhibitor Ly294002 (1.0 $\mu M$, 0.1 $\mu M$, and 0.01 $\mu M$) and spheroid viability was assessed over a time period of 24 hours to 96 hours. Measurements of spheroid size and numbers revealed a dose dependent cytotoxic response in treated spheroids compared to untreated spheroids. At 24 hours post treatment, spheroids treated with Ly294002 at a concentration of 1.0 $\mu M$, 0.1 $\mu M$ or 0.01 $\mu M$ demonstrated an average decrease of 37.3+/−8.4%, 22.0+/−10.9% and 17+/−12.5% in size, respectively, compared to untreated spheroids.

At 48 hours post treatment, spheroid size decreased on average 51.2+/−6.73%, 32.6+/−5.97% and 28.9+/−9.3%, respectively, and at 96 hours post treatment, cells treated with 0.01 $\mu M$ decreased 63+/−5.9% while those treated with 1.0 $\mu M$, 0.1 $\mu M$ of inhibitor appeared dead. Spheroid numbers decreased significantly from 37.4+/−3.8%, 26.8+/−4.38% and 14.5+/−8.52%, respectively, at 24 hours post treatment to 61.7+/−2.92%, 52.6+/−2.93% and 40.3+/−2.44%, respectively, at 48 hours. Spheroids treated with 0.01 $\mu M$ inhibitor decreased by 93.3+/−0.48% while spheroids treated with 1.0 $\mu M$, 0.1 $\mu M$ of inhibitor dissipated at 96 hours post treatment.

Figure 6A:
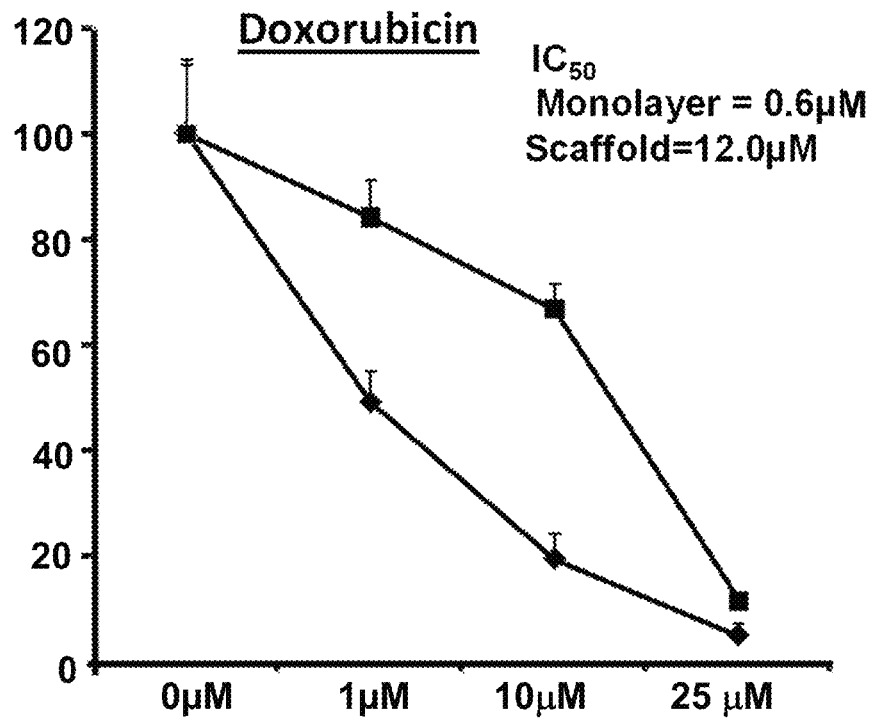
FIGS. 6A-6C show the dose dependent cytotoxic response of MCF-7 cells to inhibitors doxorubicin, LY 294002, and U0126. The IC50 of each inhibitor is shown after administration to MCF-7 cells cultured on the 3P scaffold. MCF cells (7×10$^3$) were cultured on monolayer and 3P scaffold for 7 days then treated with different concentration of LY294002 and U0126 for 48 hours. Cells were stained with calcein/am and ethydium bromide then counted. Mean percentage of live cells (+/−SEM) were plotted as a function of drug concentration on and represents 4 replicates in 3 separate experiments. Box data points indicate monolayer and diamond data points indicate 3P scaffold.
Figure 6B:
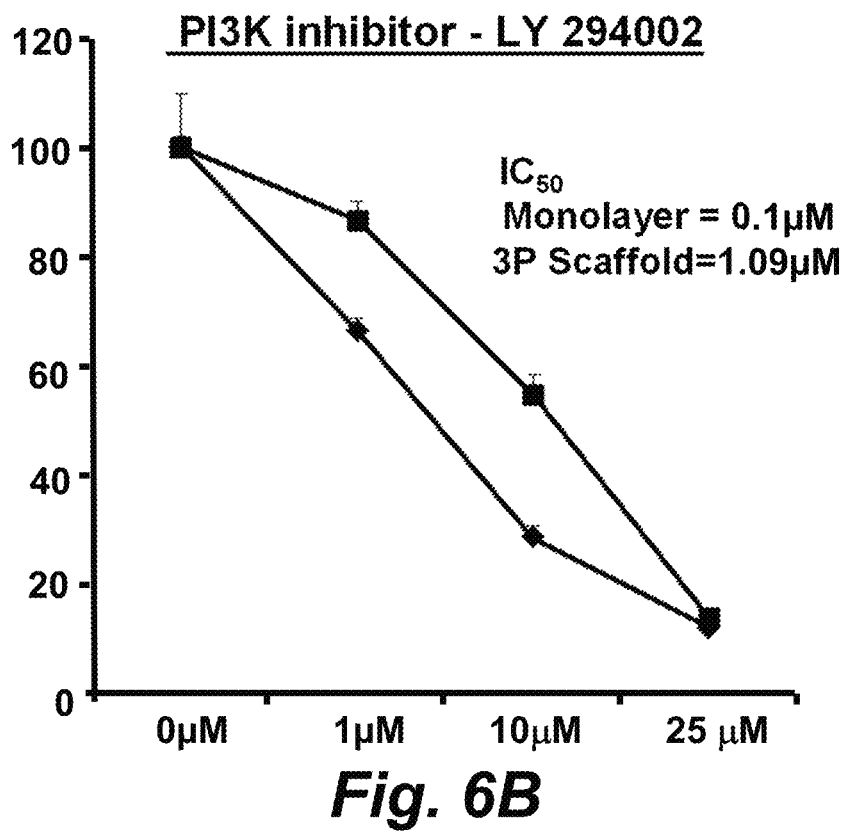
Figure 6C:
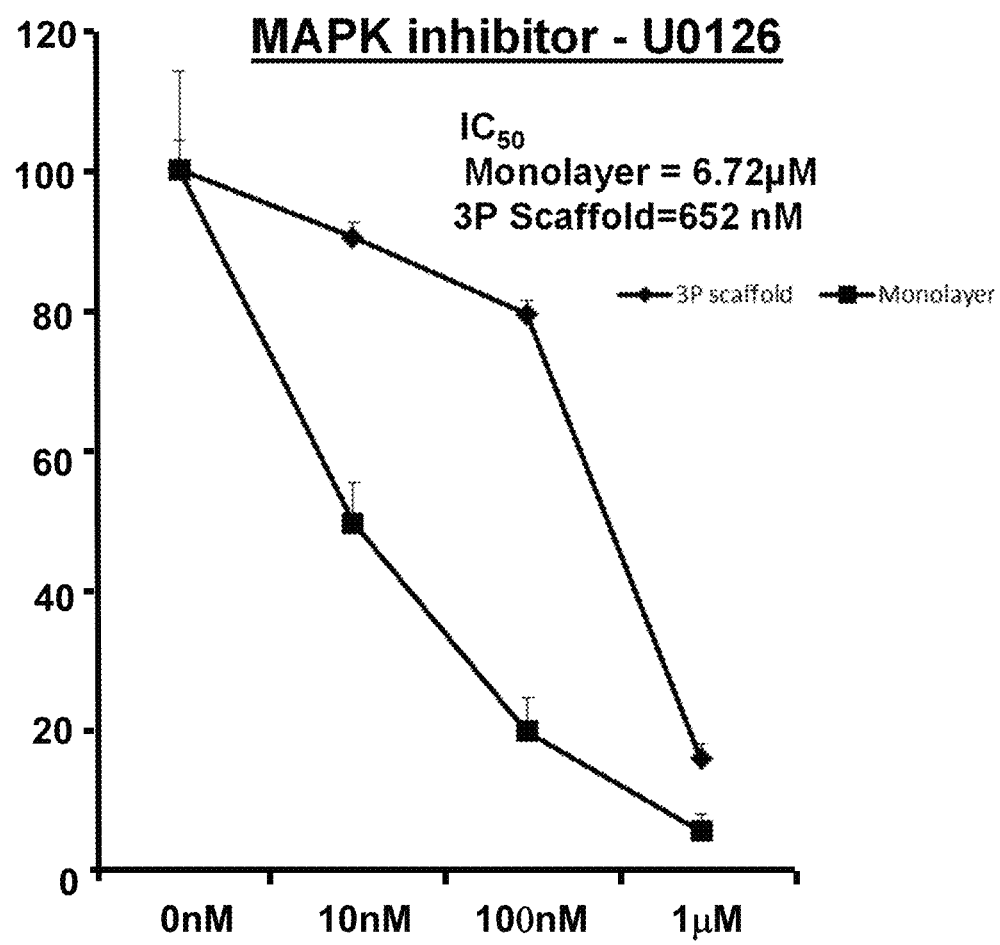
Figure 7A:
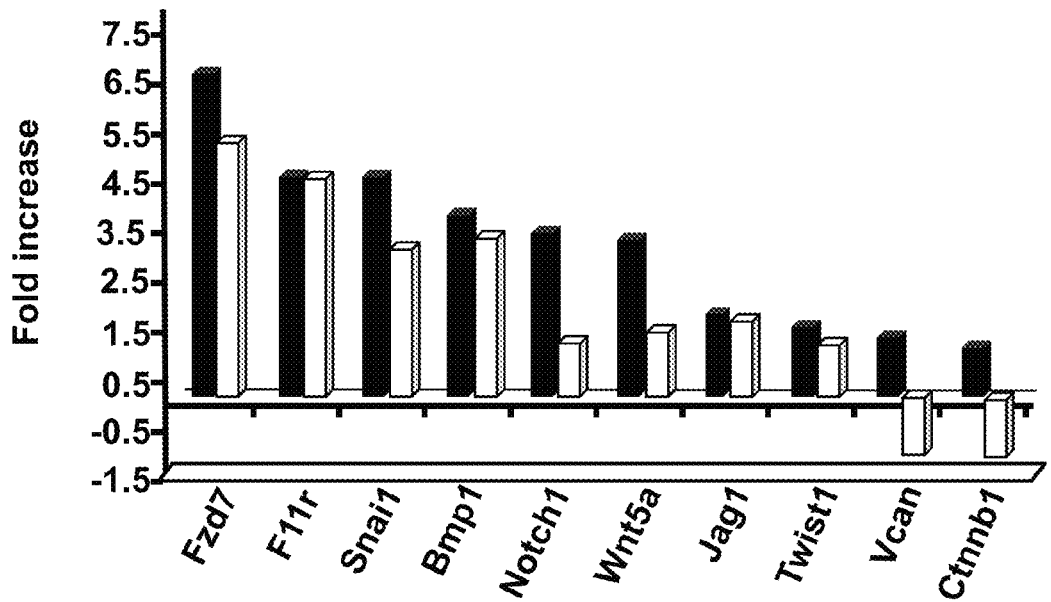
FIGS. 7A-7B show graphs showing the comparison of EMT gene expression associated with 3D vs. 2D culture. Gene expression differences in cells cultured on 3P scaffold vs. monolayer (2D) and 3P scaffold vs. PLGA (3D) at 48 hours culture. Shown are a selected group of genes that showed a greater than one-fold difference in differentiation and development (FIG. 7A) and cell growth and proliferation (FIG. 7B).
Figure 7B:
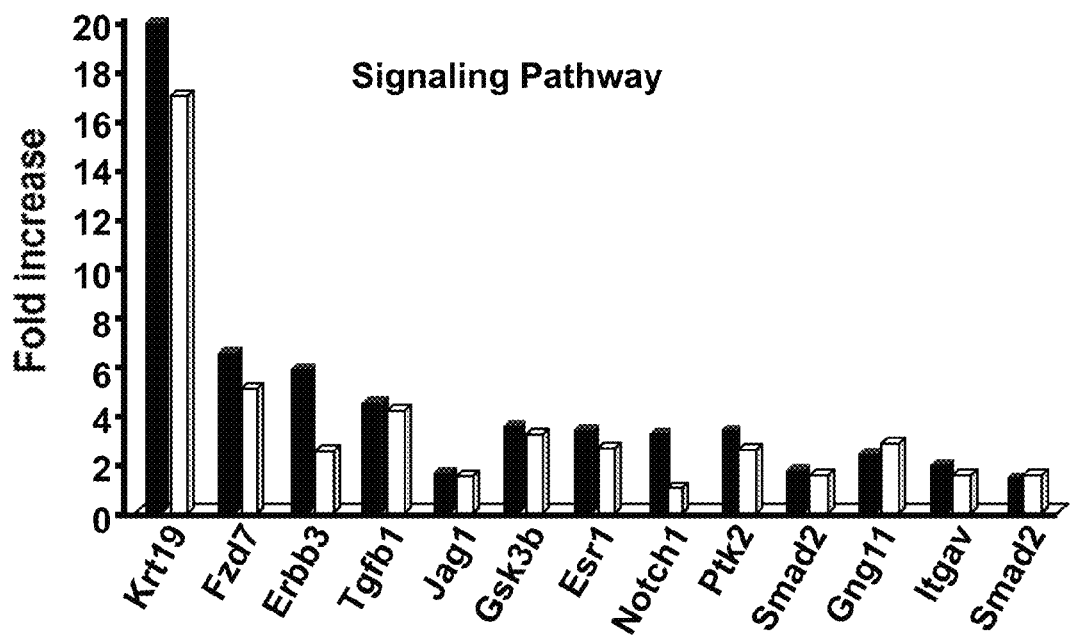
Figure 8A:
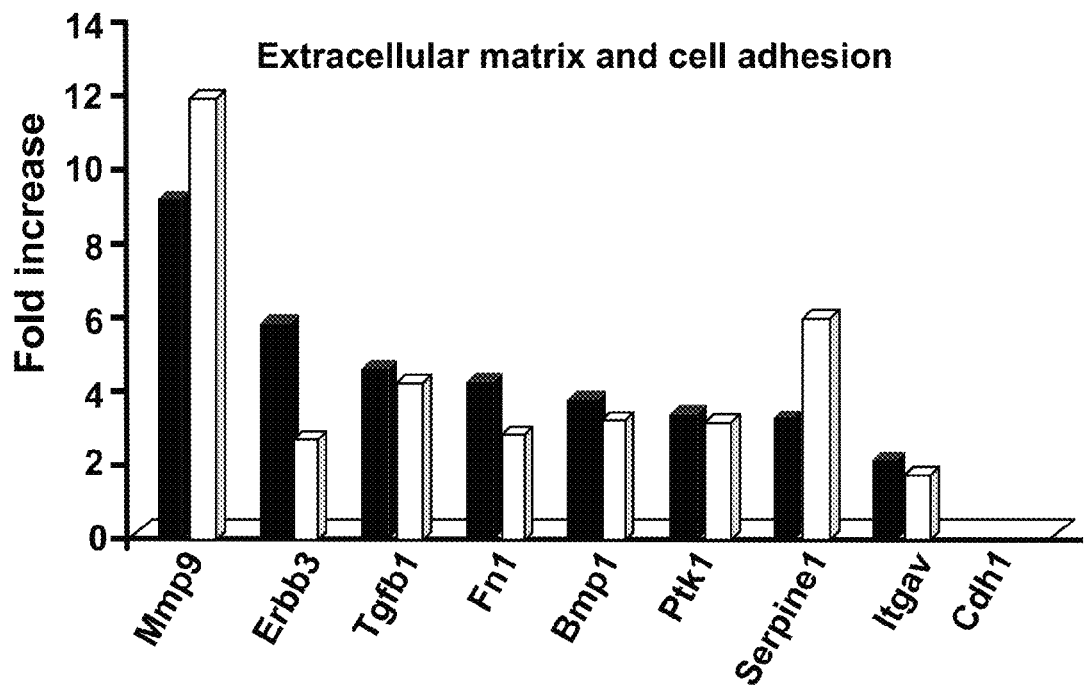
FIGS. 8A-8B provide graphs showing the comparison of EMT gene expression associated with 3D vs. 2D culture. Gene expression differences in cells cultured on 3P scaffold vs. monolayer (2D) and 3P scaffold vs. PLGA (3D) at 48 hours culture.
Figure 8B:
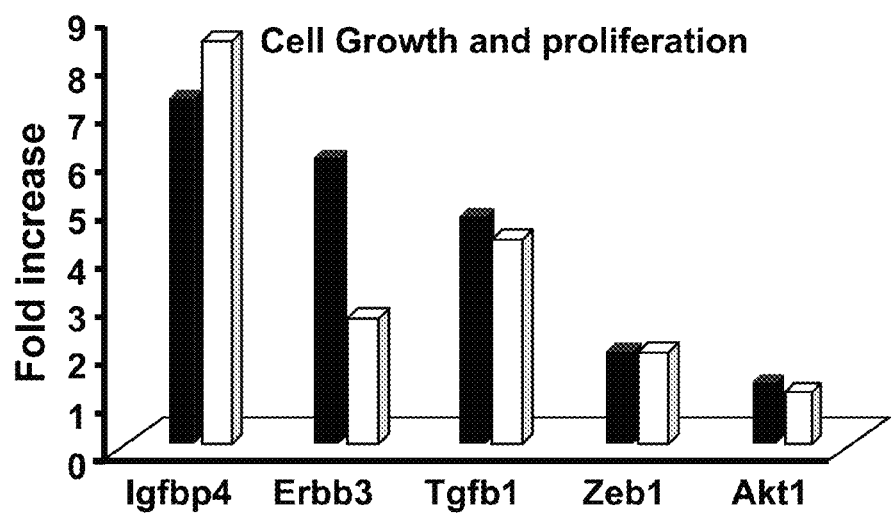
Figure 9:
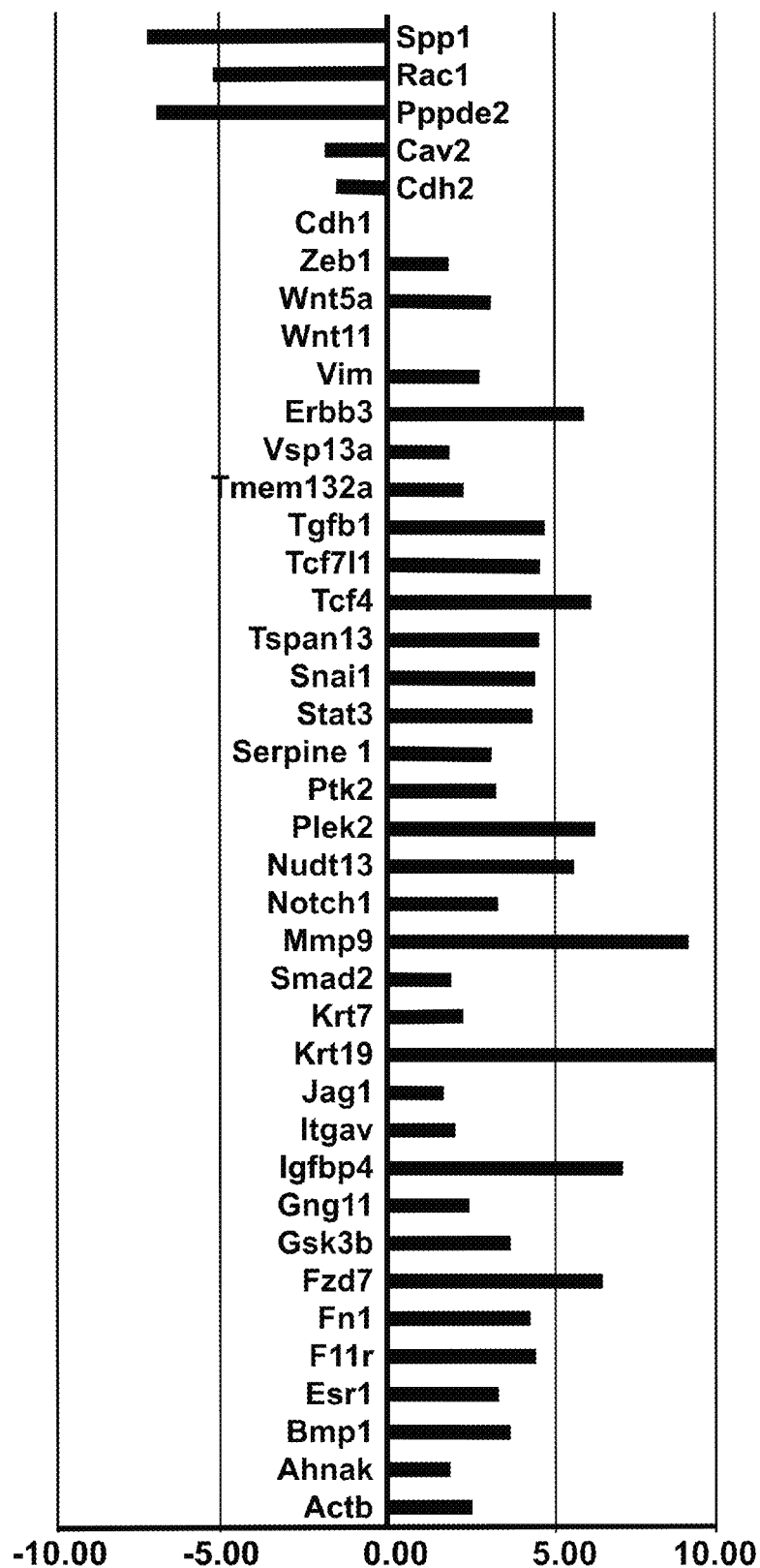
FIG. 9 provides a graph showing EMT gene expression associate with growth of tumor spheroids on 3P scaffold versus monolayer after 2 days.
Figure 10:
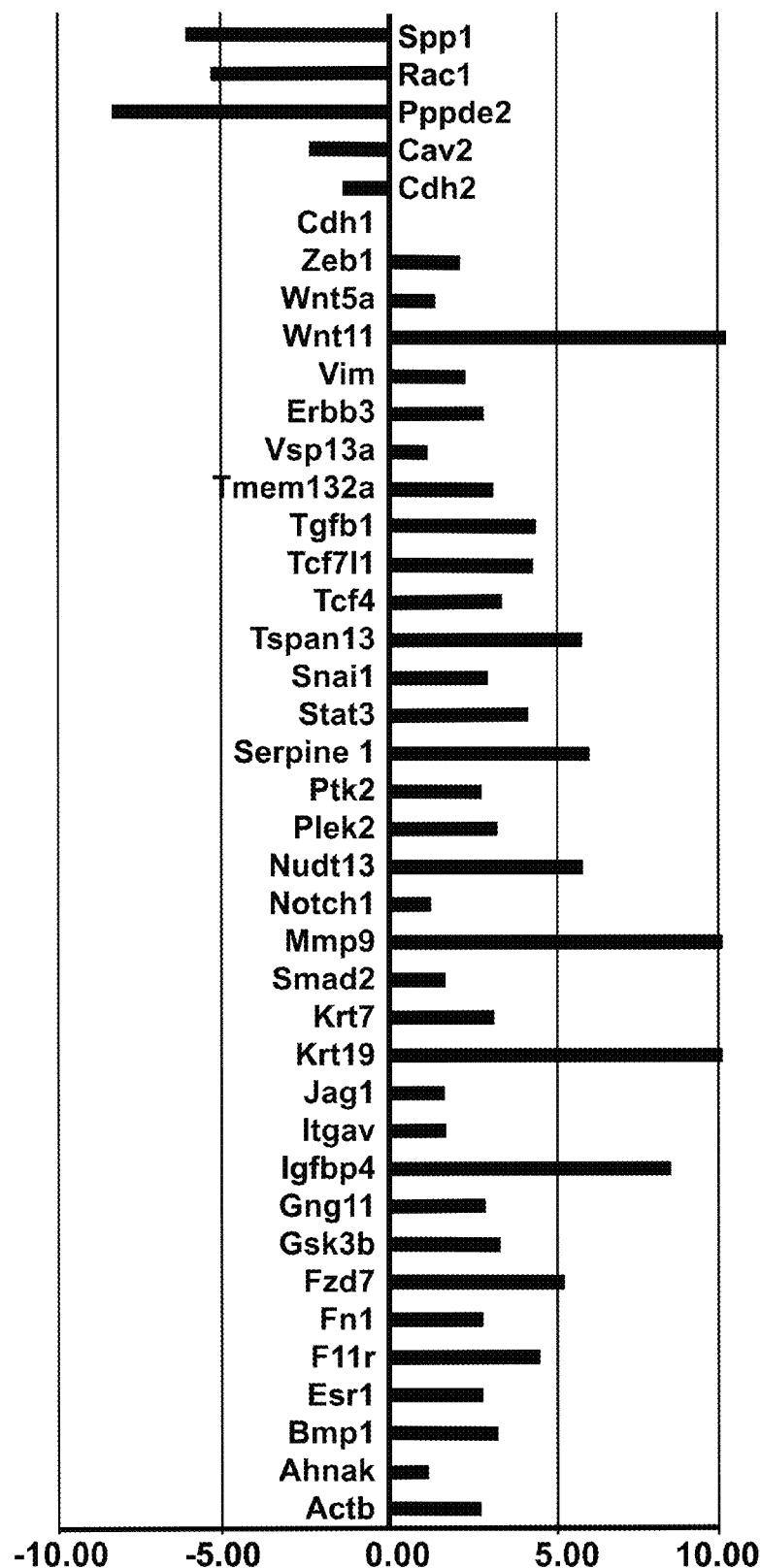
FIG. 10 provides a graph showing EMT gene expression associate with growth of tumor spheroids on 3P scaffold versus PLGA after 2 days.
Figure 11:
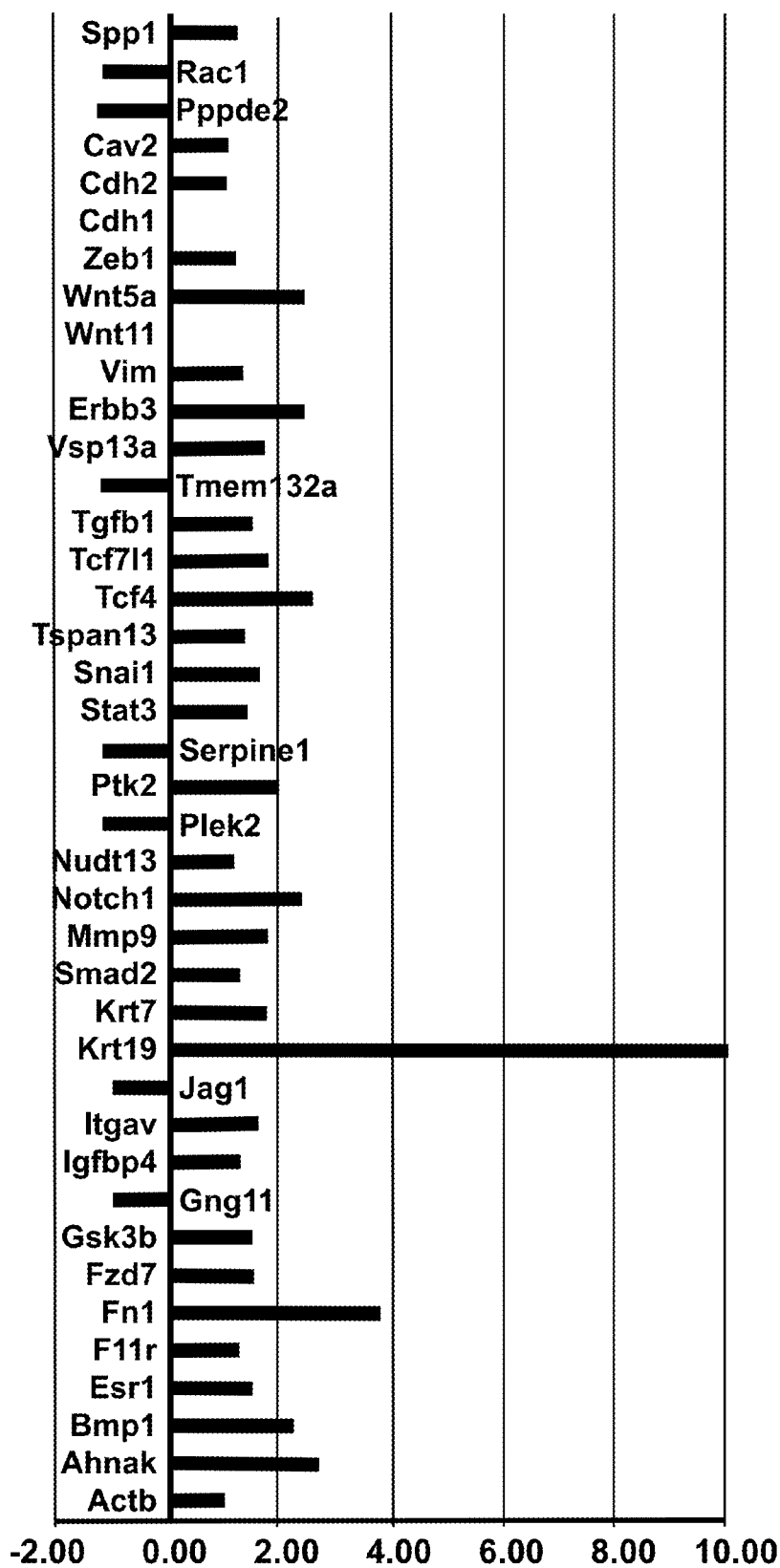
FIG. 11 provides a graph showing EMT gene expression associate with growth of tumor spheroids on 3P scaffold versus monolayer after 3 days.
Figure 12:
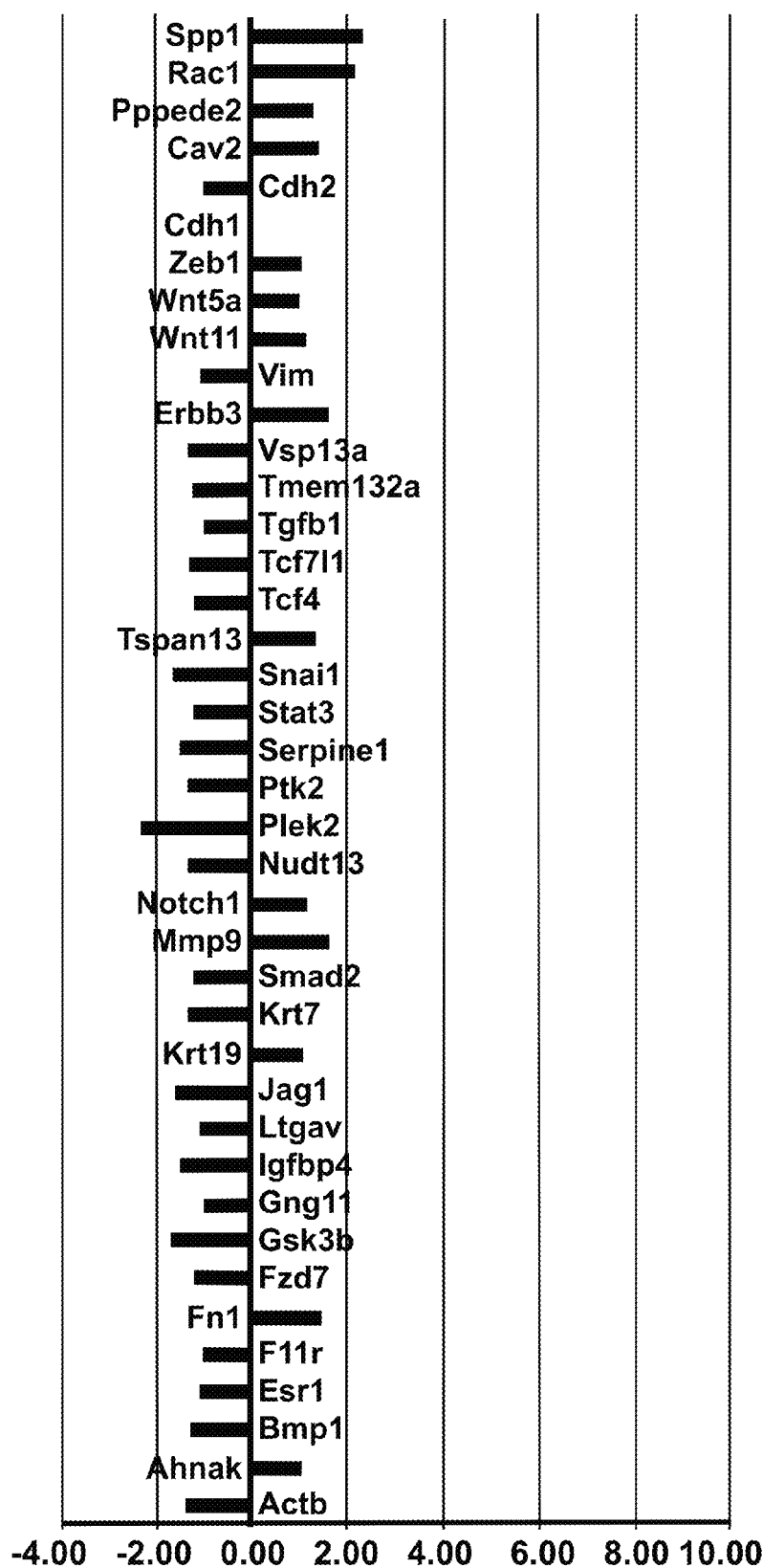
FIG. 12 provides a graph showing EMT gene expression associate with growth of tumor spheroids on 3P scaffold versus PLGA after 3 days.
Figure 13:
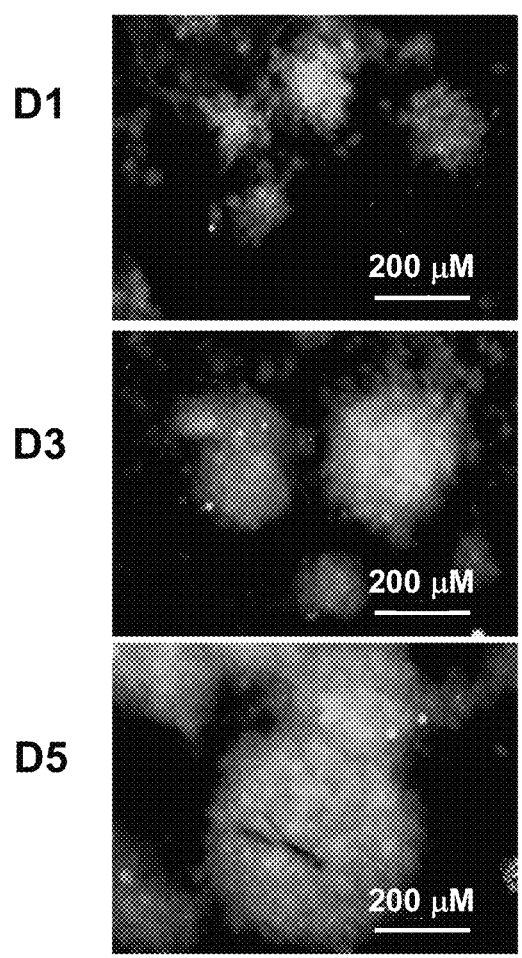
FIGS. 13-17 illustrate the culturing tumor biopsies on 3P scaffold. FNA of implanted LLC1 mouse tumors were cultured on 3P scaffolds for the indicated time.
Figure 14:
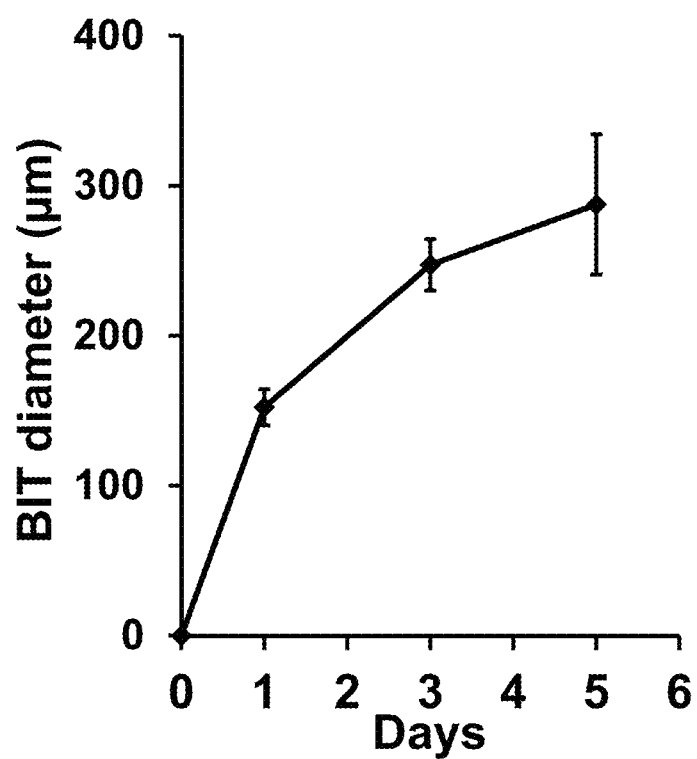
Figure 15:
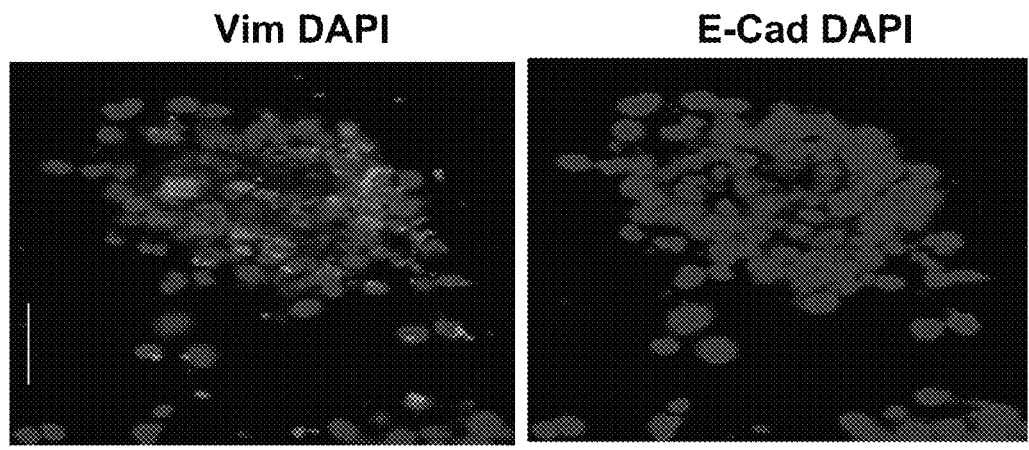
Figure 16:
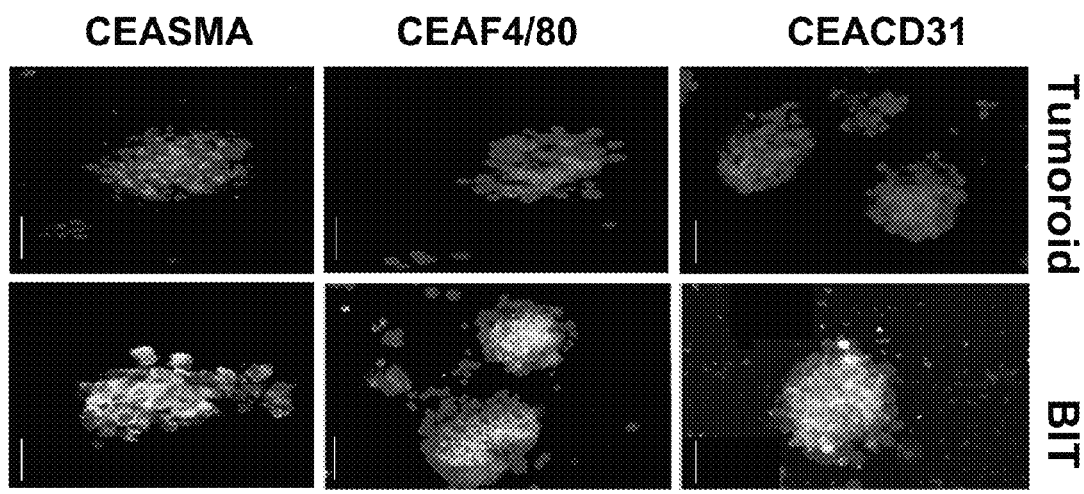
Figure 17:
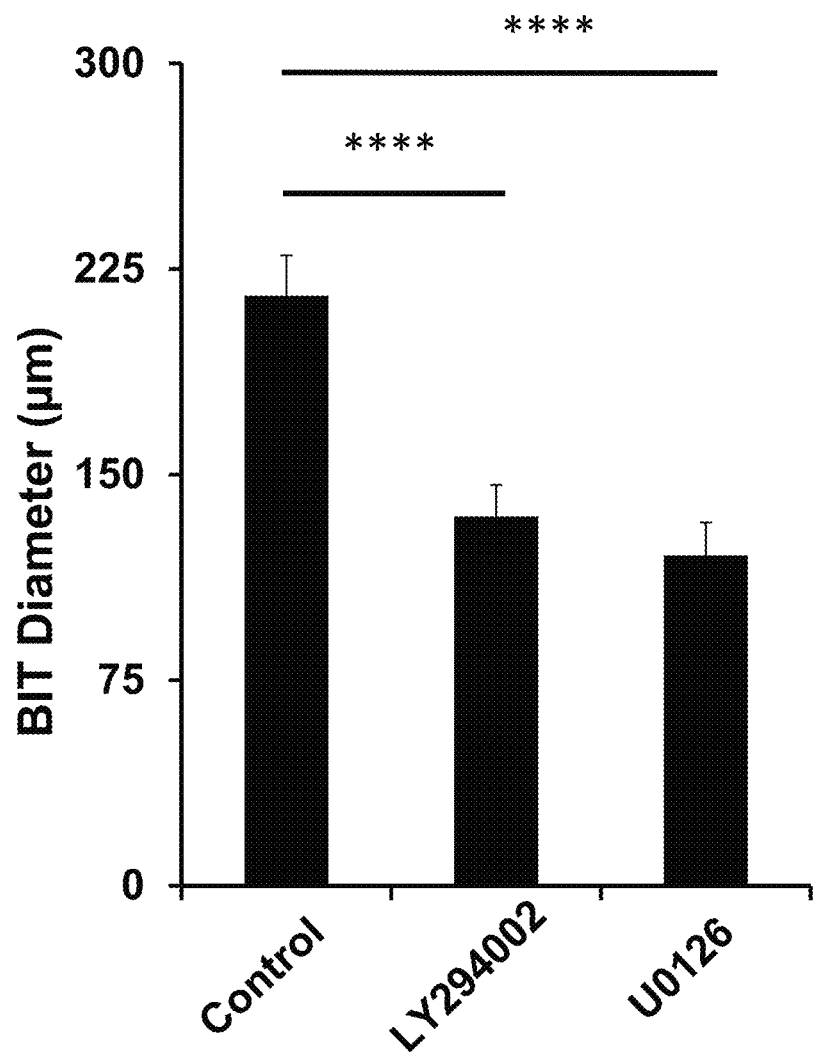

To further explore the utility of the 3P scaffold as a tool to monitor chemotherapeutic prevention of EMT, MCF-7 breast cancer cells were treated with Doxorubicin and Ly294002 and U0126 inhibitors to prevent spheroid formation and examined for a differential dose-dependent response which was compared with response in monolayer 2D culture. As mentioned previously, treatment of MCF-7 spheroids with inhibitors abrogated spheroid formation and on the 3P scaffold. The IC-50 of a drug is defined as the median lethal dose of a drug to inhibit biological or biochemical function. Successive viability measurements of treated cells revealed significantly different cytotoxic responses between cells on the 3P scaffold and on monolayer culture. After 48 hours of drug induction, MCF-7 cell viability was significantly lower and indicated a higher sensitivity in 2D monolayer culture than cells cultured on the 3P scaffold. The IC-50 of doxorubicin on monolayer was 0.6 $\mu M$ and on 3P scaffold was 12.0 $\mu M$. The IC-50 of U0126 on the monolayer was 10.6 nm, whereas the IC-50 U0126 on the 3P scaffold 105.9 nm. The IC-50 for LY294002 for the monolayer was 0.13 $\mu M$, while it was 1.15 $\mu M$ for the 3P scaffold (FIG. 6A-C).

It has been proposed that decreased sensitivity to anti-cancer drugs in spheroid cultures may be attributed to factors related to micro environmental mechanisms operating at the multicellular level as well as a function of the synthetic in vitro 3D conditions. Since these factors may limit drug penetration into the interior of the spheroid, the intrinsic auto florescent ability of doxorubicin was utilized to evaluate if diffusion limitations were a factor in drug resistance. After incubating MCF-7 spheroids on the 3P scaffold for 2 hours in the presence of 10 $\mu M$ doxorubicin, it was observed that the drug completely penetrated the spheroid in 2 hours (data not shown) suggesting that drug resistance in the 3P system cannot merely be explained by effects on drug transport.

Example 7

Gene expression analysis: EMT is a key process that is implicated in tumor metastasis, and potentially involves a global change in gene expression. Since spheroid formation induced EMT on the 3P scaffold and not on PLGA or monolayer culture, gene expression analysis was performed to determine the underlying molecular mechanisms involved. In this analysis, a focused EMT microarray was used to test for expression of 84 genes encoding cell surface receptors, extracellular matrix proteins, cytoskeletal proteins that mediate cell migration, motility, and morphogenesis; proteins that control cell differentiation, development, growth and proliferation; as well as signal transduction and transcription factor proteins that contribute to EMT and all its associated processes.

Total RNA was isolated from LLC cells cultured on the 3P scaffolds, PLGA scaffolds, and monolayers at 48 hours. A one-fold expression was used to assess the differences between LLC cells grown as spheroids on 3P versus PLGA and 3P versus monolayer and presented them in the ontological groupings described above. The number of genes up regulated at 48 hours was higher than down regulated genes from the same time period. Of the genes analyzed, 79% were up regulated while 21% were down regulated for the 3P versus monolayer while 60.6% were up regulated and 39.4% were down regulated for the 3P versus PLGA. (FIGS. 7-12).

The levels of gene expression depended on the culture conditions and biological classification. For example, there appears to be greater fold differences in EMT differentiation and developmental genes, between cells cultured on 3P scaffold versus monolayer and cells cultured on 3P versus PLGA as compared to differences observed in the other groups of genes. Since EMT is a trans-differentiation program, these results support the observation that the 2D monolayer environment exerts less pressure on LLC cells to undergo differentiation while combined cues from the 3P scaffold coupled with the multicellular spheroid facilitate EMT induction.

EMT involves multiple intracellular signal transduction pathways that form highly interconnected networks. Here the network pathways highlight the expected relationships between differentially expressed genes. The transcriptional repression of key epithelial markers such as E-cadherin (Cdh1), and up regulation of mesenchymal markers such as vimentin (Vim) and fibronectin (Fn1) were observed. EMT is a continuum whereby induction of genes appears to occur 24 hours prior to the expression of related proteins as observed in 48 hours in the timeline experiment described above. Up regulation of the TGF-β, Notch and WNT genes was observed, which genes drive the three major pathways that control EMT expression and are responsible for activating key mediators such as Stat3, Gsk3b, and transcription factors Twist and Snail. Since there is a network of transcriptional control regulators, other transcription factors such as transcription factors 1 and 4 (TCF11 and TCF4) and estrogen receptor1 (ESR1) would also be affected. Activation of these pathway genes further regulate the expression of genes that play a role in extracellular matrix and cell adhesion, integrin (Itgav) and metalloprotease (MMP9), and genes involved in cytoskeletal remodeling such as keratin (Krt7) and pleckstrin homology (Plek2).

Example 8

Characterization of 3PC Scaffolds: SEM showed that tumor cells maintained their basic morphology when grown on the electrospun 3PC scaffolds. Further, a Ki-67 assay and a viability assay showed that tumor cells proliferate and remain viable when grown on the 3PC scaffolds (for up to three days). Tumor cells grown on 3PC scaffolds were less sensitive to doxorubicin compared to cells grown on monolayer, suggesting that results from 2D studies cannot be relied upon. It was also determined that PLGA naked scaffolds are biocompatible and show increased tumorigenesis potential. From these observations, one can conclude that these 3D matrices can be used as a model to study cancer.

Example 9

Culturing fine needle aspirates (FNAs) of implanted mouse tumors: LLC1 cells ($5 \times 10^5$) were subcutaneously injected into the flanks of wild type C57BL/6 mice (National Cancer Institute). Tumor formation was monitored for 2 weeks after which tumor biopsies were collected by fine needle aspiration. Briefly, a 23-gauge needle was inserted into the tumor using a rotating motion and the tissue samples were flushed from the needle by attaching a syringe filled with tissue culture medium and expelling the contents into a sterile tube. This process was repeated twice. The three collected tumor samples were pooled and single cell suspensions were cultured on the scaffold.

Chemosensitivity of tumor biopsies grown on 3P scaffolds: To determine if the 3P scaffold can be utilized to culture tumor biopsies, single-cell suspensions of FNAs of implanted mouse tumors were cultured on 3P scaffolds. As shown in FIGS. 6A and 6B, the average diameter of biopsy induced tumoroids (BITs) increased from day 1 to day 5 at approximately the same rate as observed in the experiments with tumor cell lines. Immunostaining of BITs showed loss of expression of E-cadherin and gain of expression of vimentin suggesting EMT induction (FIG. 6C). In addition to tumor cells, BITs were examined for the presence of stromal cells that are typical of in vivo tumor microenvironment (TME) (Mallela et al., (2013) Stem Cells 31: 1321-1329) by immunostaining with antibodies to respective cell surface markers.

BITs were found positive for the tumor cell marker, carcinoma embryonic antigen (CEA), macrophage marker F4/80, endothelial progenitor cell marker CD31 and cancer associated fibroblast marker smooth muscle actin (SMA), indicating the presence of stromal components of the TME (FIG. 6D). LLC1 tumoroids, used as control expressed only CEA.

To determine if the biopsy tumoroids cultured on 3P scaffolds can be utilized to assess drug sensitivity, FNA tumoroids were cultured in the presence or absence of the inhibitors, LY294002 and U0126. Results showed that inhibitors were effective in modulating growth of BITs as revealed by decreases in tumoroid size and a dose-dependent cytotoxicity. However, the $IC_{50}$s of LY294002 and U0126 were greater than 1 mM (FIG. 6E) indicating a greater resistance of BITs to the drugs than were the LLC1-based tumoroids. Increased drug resistance of biopsy tumoroids in the 3P system was not due to a lack of drug uptake.

The present disclosure encompasses embodiments of a 3P fibrous scaffold that induces the formation of a micrometastatic compact aggregate of tumor cells that is termed a 'tumoroid'. Cancer cells seeded onto these scaffolds with growth medium containing the appropriate factors grow as tumoroids that show the EMT characteristic of in vivo tumorigenesis. In addition, this platform further allows the co-culture of tumor cells and stromal cells to identify changes in specific factors, gene expression and invasion potential.

Tumoroids are able to respond to the same biochemical, nanotopographical and mechanical cues that drive tumor progression in the native ECM (Fischbach et al., (2007) Nat. Methods 4: 855-860). The 3P platform of the disclosure can be used to evaluate therapeutic strategies for simultaneously targeting tumor cells and the stromal cells that are components of the stem cell niche (Ballangrud et al., (1999) Clin. Cancer Res. 5: 3171s-3176s). The 3P platform can further be adapted for use in a point-of-care device to culture a patient's own cells from a biopsy, test them ex vivo with different anticancer compounds and tailor a personalized treatment by selecting the most effective therapeutic agent and determining an effective dose for the particular tumor cells from that patient.

Treatment of tumoroids with Ly294002 or U0126 on 3P scaffolds versus monolayer culture showed higher drug resistance of MCF7 cells when on the scaffold. The $IC_{50}$ values for 3P cultures were 10-fold higher for Ly294002 inhibitor and 100-fold higher for U0126 inhibitor than for monolayer cultures. These results are similar to other reports by other studies showing that tumor cells grown as 3D tumoroids develop multicellular resistance to most cytotoxic drugs compared to those grown in monolayer culture (Kobayashi et al., (1993) Proc. Natl. Acad. Sci. USA 90: 3294-3298; Desoize et al., (1998) Bull. Cancer 85: 785). For example, the in vivo drug-resistant variant, EMT-6, of mouse mammary tumor cells lost resistance when cultured as a monolayer but regained it when regrown in vivo as a solid tumor or in vitro as tumoroids (Teicher et al. (1990) Science 247: 1457-1461). The reasons for the differences between 3D and monolayer cultures remain unknown.

Pathophysiological gradients to nutrients, oxygen and drugs and the concentric arrangement of heterogeneous cell populations within the 3P tumoroids may affect RNA and protein expression. For example, it has been reported that quiescent cells near the necrotic core of a tumoroid up-regulate the cyclin-dependent kinase inhibitor p27Kip1, which arrests cells in the G0/G1 phase and induces cell cycle resistance (St Croix et al. (1996) *Nat. Med.* 2: 1204-1210). The expression of p27Kip1 is fifteen times greater in tumoroid culture than in monolayer culture. In addition, inhibition of apoptosis via the Bcl-2 pathway (Zhang et al., (1995) *Proc. Natl. Acad. Sci. USA.* 92: 6161-6165) and the down-regulation of PMS2 and topoisomerase 11 DNA mismatch repair proteins (Francia et al., (2004) *Mol. Cell Biol.* 24: 6837-6849; Olive et al., (1991) *Int. J. Radiat. Biol.* 60: 453-466) have been proposed as mechanisms that desensitize tumor cells in tumoroids to antitumor agents. It has now been found that this resistance was not a result of a mass transport defect. This is consistent with other drug penetration data that have shown that despite efficient drug penetration, tumoroids still exhibit higher drug resistance than monolayer cultures (Erlanson et al., (1992) *Cancer Chemotherapy Pharmacol.* 29: 343-353; Ho et al. (2010) *Cancer Sci.* 101: 2637-2643). These data demonstrate that tumoroid growth on 3P scaffolds reflects physiological growth conditions in which changes in cell phenotype and signaling add significant cues for the regulation of cell behavior and drug resistance.

Tumor-stroma interactions affect cancer growth, differentiation, metastasis and the acquisition of drug resistance. To determine if the 3P scaffold of the disclosure was an appropriate in vitro model for anticancer drug screening tumor biopsy specimens were cultured on the scaffold. 3P scaffolds supported the growth of both tumor and stromal cells from the biopsy and this in vitro platform therefore mimics in vivo tumor growth. Moreover, it was unexpectedly found that tumoroids derived from the biopsies (BITs) were more resistant to MEK and PI3K inhibitors than the tumoroids from cancer cell lines.

Accordingly, while tumoroids derived from a cell line exhibit a distinct drug sensitivity profile, they do not accurately reflect the in vivo condition. Results with the biopsy-derived tumoroids cultured on the 3P scaffold of the disclosure, however, suggest that co-cultures of tumor cells with stromal cells, as obtained from the biopsied tumors will produce tumoroids that better reflect the in vivo context. These tumor/stroma effects on chemosensitivity underscore the advantage of using a 3D platform such as the 3P scaffold for growth of actual patient tumor biopsies to test the efficacy of anticancer drugs.

The scaffold-based platform of the disclosure, therefore, provides an approach useful for developing customized, or personalized, anticancer treatments. Thus, it is contemplated that tumor biopsies can be cultured on a 3P scaffold, differentiated into BITs and then screened with an array of anticancer drugs to determine the most effective drug combinations for a particular cancer patient. Such results can be obtained within a week.

Rapid advances in genetics, genomics and related technologies are promising a new era of personalized cancer therapy based on molecular characterization of a patient's tumor and its microenvironment with the intent to improve outcomes and decrease toxicity [85]. The heterogeneity of tumors, the lack of effective drugs against most genomic aberrations and the technical limitations of molecular tests hamper the current approaches for predicting the response to anticancer drugs. The 3P scaffold are useful for drug screening and customized cancer therapy by providing tumoroids that closely mimic the physiological and pharmaceutical responses seen in a tumor within an affected animal.

What is claimed:

1. A three-dimensional scaffold composition consisting of a three-dimensional scaffold of randomly oriented electrospun nanofibers, wherein the electrospun nanofibers consist of polyethylene glycol-polylactic acid block copolymer (PEG-PLA) and poly(lactic-co-glycolic acid) (PLGA), wherein ratio of PEG-PLA to PLGA is approximately 1:4 with fiber diameter ranges from approximately 0.69 to 4.18 micrometers and with pores having a diameter of less than approximately 10 micrometers, and a population of cells that have undergone an endothelial-mesenchymal transition to form a tumoroid.

2. The composition of claim 1, wherein the PEG has a molecular weight of about 2 kDa.

3. The composition of claim 1, wherein the PLGA has a lactic acid:glycolic acid ratio of about 85:15.

4. The composition of claim 1, wherein the population of cells comprises a population of cancerous cells and stromal cells isolated from a tumor of an animal or human subject.

5. A method of generating a tumoroid comprising inoculating the scaffold of claim 1 with a population of cells that have been removed from an animal or human tumor and not previously incubated in cell culture medium and generating a tumoroid by incubating the inoculated scaffold in a cell culture medium under conditions allowing for proliferation of the cells.

6. The method of claim 5, wherein the population of cells inoculated onto the scaffold comprises a mixture of cancerous cells and stromal cells isolated from a tumor of an animal or human subject.

7. A method of identifying a compound that modulates the proliferation of cells of a tumor of an animal or human, comprising inoculating the scaffold of claim 1 with a population of cells that have been removed from an animal or human tumor and not previously incubated in cell culture medium and generating a tumoroid by incubating the inoculated scaffold in a cell culture medium under conditions allowing proliferation of the cells; contacting the tumoroid with a compound suspected of modulating the proliferation of the cells of the tumoroid; comparing the proliferation of the cells of the tumoroid in contact with said compound with the proliferation of cells of a tumoroid not in contact with said compound, thereby determining if the compound modulates the proliferation of the cells of the tumoroid.

8. The method of claim 7, wherein the population of cells inoculated onto the scaffold comprises a mixture of cancerous cells and stromal cells.

* * * * *